(12) United States Patent
Shimizu et al.

(10) Patent No.: US 12,097,510 B2
(45) Date of Patent: Sep. 24, 2024

(54) AIR CLEANER, AIR CLEANER SYSTEM, AND AIR-CONDITIONING APPARATUS

(71) Applicant: Mitsubishi Electric Corporation, Tokyo (JP)

(72) Inventors: Akinori Shimizu, Tokyo (JP); Akane Nomura, Tokyo (JP); Yasuhiro Nakamura, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 18/689,450

(22) PCT Filed: Sep. 24, 2021

(86) PCT No.: PCT/JP2021/034959
§ 371 (c)(1),
(2) Date: Mar. 6, 2024

(87) PCT Pub. No.: WO2023/047509
PCT Pub. Date: Mar. 30, 2023

(65) Prior Publication Data
US 2024/0261799 A1 Aug. 8, 2024

(51) Int. Cl.
*B03C 3/68* (2006.01)
*A61L 9/22* (2006.01)
(Continued)

(52) U.S. Cl.
CPC ...... *B03C 3/68* (2013.01); *A61L 9/22* (2013.01); *B01D 46/0028* (2013.01);
(Continued)

(58) Field of Classification Search
CPC ....... F24F 8/26; F24F 8/30; F24F 8/80; Y02A 50/20; A61L 9/22; B01D 46/0028;
(Continued)

(56) References Cited

U.S. PATENT DOCUMENTS 6,984,987 B2 * 1/2006 Taylor .................. C01B 13/115
324/509
7,300,499 B1 * 11/2007 Fleisher ................ B03C 3/155
422/186.04
(Continued)

FOREIGN PATENT DOCUMENTS

CN 1522764 A 8/2004
JP H07275736 A * 10/1995
(Continued)

OTHER PUBLICATIONS

International Search Report and Written Opinion mailed on Nov. 30, 2021, received for PCT Application PCT/JP2021/034959, filed on Sep. 24, 2021, 12 pages including English Translation.
(Continued)

*Primary Examiner* — Christopher P Jones
*Assistant Examiner* — Sonji Turner
(74) *Attorney, Agent, or Firm* — XSENSUS LLP

(57) ABSTRACT

An air cleaner includes: a generation unit configured to discharge an electric current by being applied with a high voltage, and generate a plurality of types of discharge products; an air-sending device configured to form a flow of air, and spray the plurality of types of discharge products generated from the generation unit to a space; an estimation unit configured to estimate an amount of dust floating in the space by selecting whether an amount of dust floating in the space is a first estimation amount smaller than a predetermined threshold or is a second estimation amount larger than or equal to the predetermined threshold and larger than the first estimation amount; and a control unit configured to control a generation amount of the plurality of types of discharge products to be generated from the generation unit based on the amount of dust estimated by the estimation unit.

11 Claims, 9 Drawing Sheets

(51) Int. Cl.
*B01D 46/00* (2022.01)
*B01D 46/42* (2006.01)
*B01D 46/44* (2006.01)
*B01D 46/46* (2006.01)
*B03C 3/011* (2006.01)
*B03C 3/04* (2006.01)
*B03C 3/155* (2006.01)
*B03C 3/36* (2006.01)
*B03C 3/38* (2006.01)
*B03C 3/41* (2006.01)

(52) U.S. Cl.
CPC ..... *B01D 46/0032* (2013.01); *B01D 46/0047* (2013.01); *B01D 46/4263* (2013.01); *B01D 46/442* (2013.01); *B01D 46/46* (2013.01); *B03C 3/011* (2013.01); *B03C 3/04* (2013.01); *B03C 3/155* (2013.01); *B03C 3/368* (2013.01); *B03C 3/38* (2013.01); *B03C 3/41* (2013.01); *A61L 2209/111* (2013.01); *A61L 2209/134* (2013.01); *A61L 2209/14* (2013.01); *B01D 2273/30* (2013.01); *B01D 2279/65* (2013.01); *B03C 2201/06* (2013.01); *B03C 2201/24* (2013.01)

(58) Field of Classification Search
CPC ............ B01D 46/0032; B01D 46/0047; B01D 46/4263; B01D 46/442; B01D 46/46; B01D 2279/30; B01D 2279/65; B03C 3/68; B03C 3/011; B03C 3/04; B03C 3/155; B03C 3/368; B03C 3/38; B03C 3/41; B03C 2201/06; B03C 2201/24
See application file for complete search history.

(56) References Cited

U.S. PATENT DOCUMENTS

| | | | | |
|---|---|---|---|---|
| 7,371,354 B2 * | 5/2008 | Lau | ............................ | A61L 9/22 96/24 |
| 7,833,322 B2 * | 11/2010 | Botvinnik | .................. | B03C 3/68 96/24 |
| 9,427,746 B2 * | 8/2016 | Au | ............................ | B03C 3/34 |
| 10,661,637 B2 * | 5/2020 | Kwon | ....................... | B03C 3/32 |
| 2006/0024197 A1 * | 2/2006 | Park | ........................... | A61L 9/22 422/186.07 |
| 2006/0075893 A1 | 4/2006 | Kim et al. | | |
| 2006/0078482 A1 * | 4/2006 | Kim | ......................... | A61L 9/015 422/186.07 |
| 2011/0073686 A1 * | 3/2011 | Uegaki | ................. | B60H 3/0071 239/690 |
| 2013/0020497 A1 | 1/2013 | Suda et al. | | |
| 2017/0217284 A1 | 8/2017 | Ji et al. | | |
| 2018/0064840 A1 | 3/2018 | Saiki et al. | | |
| 2023/0151985 A1 * | 5/2023 | Tomimatsu | ............. | B03C 3/019 422/4 |

FOREIGN PATENT DOCUMENTS

| | | | |
|---|---|---|---|
| JP | H07-301482 | A | 11/1995 |
| JP | 2003-056878 | A | 2/2003 |
| JP | 2004-033875 | A | 2/2004 |
| JP | 2006-046821 | A | 2/2006 |
| JP | 2011-229818 | A | 11/2011 |
| JP | 2014-074505 | A | 4/2014 |
| JP | 2014-202421 | A | 10/2014 |
| JP | 2015-161478 | A | 9/2015 |
| JP | 2018-132246 | A | 8/2018 |
| JP | 2020-041750 | A | 3/2020 |
| JP | 6698973 | B1 * | 5/2020 |
| KR | 10-2003-0071677 | A1 | 9/2003 |
| WO | 2016/157383 | A1 | 10/2016 |

OTHER PUBLICATIONS

Notice of Reasons for Refusal mailed on Mar. 29, 2022, received for JP Application 2022-503947, 14 pages including English Translation.

Decision of Refusal mailed on Jul. 26, 2022, received for JP Application 2022-503947, 6 pages including English Translation.

Decision to Grant mailed on Nov. 15, 2022, received for JP Application 2022-503947, 5 pages including English Translation.

* cited by examiner

AIR CLEANER, AIR CLEANER SYSTEM, AND AIR-CONDITIONING APPARATUS

CROSS-REFERENCE TO RELATED APPLICATION

This application is based on PCT filing PCT/JP2021/034959, filed Sep. 24, 2021, the entire contents of which are incorporated herein by reference.

TECHNICAL FIELD

The present disclosure relates to an air cleaner including a generator configured to emit chemical species generated by high-voltage electric discharge, and also relates to an air cleaner system including the air cleaner, and an air-conditioning apparatus including the air cleaner.

BACKGROUND ART

There have been air cleaners with a technique to apply a high voltage between electrodes to generate and emit discharge products to the air to kill or inactivate target bacteria or viruses (see, for example, Patent Literature 1). The air cleaner described in Patent Literature 1 aims to control the balance between elements that make up the discharge products such as ions and ozone, and emit the discharge products to the target, thereby improving sterilization performance or inactivation performance compared to use of a single type of discharge products.

CITATION LIST

Patent Literature

Patent Literature 1: Japanese Unexamined Patent Application Publication No. H07-301482

SUMMARY OF INVENTION

Technical Problem

When the air cleaner described in Patent Literature 1 emits a plurality of types of discharge products to a space in which a large amount of dust is present, the discharge products come into contact with the dust. In a case of the air cleaner configured to clean air by emitting discharge products to the air, some of the discharge products come into contact with the dust, and thus bond with the dust. This results in a decrease in the number of discharge products present in the space. When the air cleaner described in Patent Literature 1 discharges an electric current to a space where there is a large amount of dust, discharge products are thus unnecessarily wasted. This causes a concern about degradation in the sterilization performance and inactivation performance.

The present disclosure has been made to solve the above problems, and it is an object of the present disclosure to provide an air cleaner, an air cleaner system, and an air-conditioning apparatus that prevent a reduction of discharge products present in a space, and exhibit adequate sterilization performance and inactivation performance.

Solution to Problem

An air cleaner according to one embodiment of the present disclosure includes: a generation unit configured to discharge an electric current by being applied with a high voltage, and generate a plurality of types of discharge products; an air-sending device configured to form a flow of air, and spray the plurality of types of discharge products generated from the generation unit to a space; an estimation unit configured to estimate an amount of dust floating in the space by selecting whether an amount of dust floating in the space is a first estimation amount smaller than a predetermined threshold or is a second estimation amount larger than or equal to the predetermined threshold and larger than the first estimation amount; and a control unit configured to control a generation amount of the plurality of types of discharge products to be generated from the generation unit based on the amount of dust estimated by the estimation unit.

An air cleaner system according to another embodiment of the present disclosure includes: the air cleaner of the above configuration; and an additional device located in the space in which the air cleaner is located. The air cleaner and the additional device include respective communication modules through which the air cleaner and the additional device are allowed to communicate with each other, and the estimation unit is configured to estimate the amount of dust in the space based on information on an operating condition of the additional device received through the communication modules.

An air cleaner system according to still another embodiment of the present disclosure includes: the air cleaner of the above configuration; and an additional device located in the space in which the air cleaner is located. The air cleaner and the additional device include respective communication modules through which the air cleaner and the additional device are allowed to communicate with each other, the additional device further includes a second dust sensor configured to measure the amount of dust in the space, and the estimation unit is configured to receive information on the amount of dust measured by the second dust sensor through the communication modules and estimate the amount of dust in the space.

An air-conditioning apparatus according to still further another embodiment of the present disclosure includes: the air cleaner of the above configuration; and a heat exchanger configured to exchange heat between refrigerant flowing inside the heat exchanger and air that is present around the heat exchanger. Air supplied by the air-sending device passes through the heat exchanger, and the air-conditioning apparatus is configured to supply the plurality of types of discharge products to the space, by use of conditioned air passing through the heat exchanger.

Advantageous Effects of Invention

According to embodiments of the present disclosure, the air cleaner, the air cleaner system, and the air-conditioning apparatus include the estimation unit configured to estimate the amount of dust floating in the space, and the control unit configured to control the generation amount of a plurality of types of discharge products to be generated from the generation unit based on the amount of dust estimated by the estimation unit. The air cleaner, the air cleaner system, and the air-conditioning apparatus control the generation amount of the plurality of types of discharge products according to the amount of dust in the space, and thereby prevent the discharge products from being unnecessarily consumed. With this operation, the air cleaner, the air cleaner system, and the air-conditioning apparatus prevent a reduction of the discharge products present in the space, and exhibit adequate sterilization performance and inactivation performance.

DESCRIPTION OF EMBODIMENTS

Figure 1:
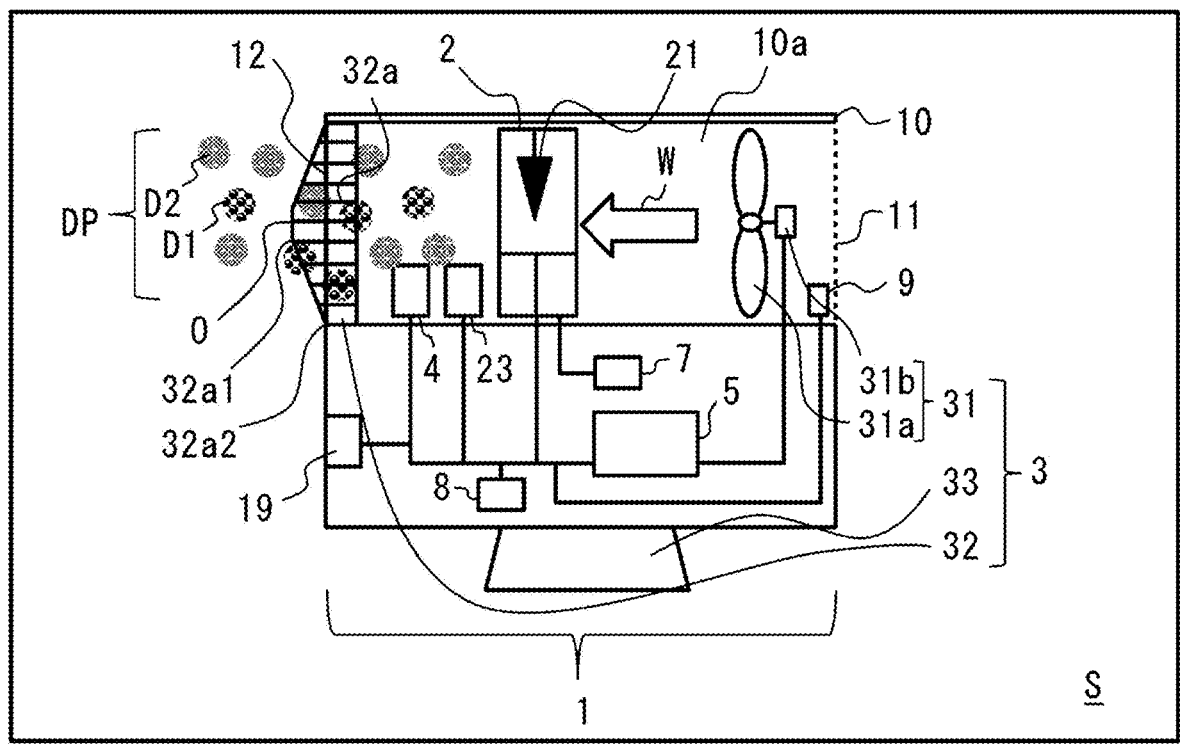
FIG. 1 is a schematic diagram illustrating an example of a relationship between an air cleaner according to Embodiment 1 and a space where the air cleaner is installed.

Hereinafter, an air cleaner according to an embodiment will be described with reference to the drawings and other reference. In the drawings below, the same reference signs denote the same or corresponding components, and are common throughout the entire descriptions of the embodiments described below. In addition, the relationship of sizes of the components in the drawings described below may differ from that of actual ones. The forms of constituent elements described throughout the entire specification are merely examples, and do not intend to limit the constituent elements to the forms described in the specification. In particular, a combination of the constituent elements is not limited to only the combination in each embodiment, and the constituent elements described in one embodiment may be applied to another embodiment.

Embodiment 1

[Overall Configuration of Air Cleaner 1]

FIG. 1 is a schematic diagram illustrating an example of a relationship between an air cleaner 1 according to Embodiment 1 and a space S where the air cleaner 1 is installed. The air cleaner 1 according to Embodiment 1 is described below with reference to FIG. 1.

The air cleaner 1 is a device having an air cleaning means described below and configured to clean air in the space S. More specifically, the air cleaner 1 is a device configured to kill or inactivate bacteria or viruses present in the space S. The air cleaner 1 is not limited to the device only having an air cleaning function, but may have a function to serve as a commonly-called air-conditioning apparatus, in addition to the air cleaning function. For example, the air cleaner 1 may have a temperature regulating function and a humidity regulating function, or may have a ventilating function.

The air cleaner 1 includes a generation unit 2 configured to generate a plurality of types of discharge products DP, an air-sending unit 3 configured to spray the discharge products DP generated from the generation unit 2 to the space S, and an estimation unit 4 configured to estimate the amount of dust in the space S where the air cleaner 1 is installed. The air cleaner 1 further includes a control unit 5 configured to control operation of the air cleaner 1 based on the amount of dust estimated by the estimation unit 4. The air cleaner 1 may further include a high-voltage conversion unit 7 configured to convert a voltage input to the air cleaner 1 to a high voltage and supply the high voltage to the generation unit 2. Furthermore, the air cleaner 1 may include a measurement unit 23 configured to measure the amount of the discharge products DP. The air cleaner 1 includes a casing 10 forming the outer shell and housing the generation unit 2, a portion of the air-sending unit 3, the estimation unit 4, the control unit 5, the high-voltage conversion unit 7, the measurement unit 23, and other units in the casing 10.

(Generation Unit 2)

The generation unit 2 discharges an electric current by being applied with a high voltage obtained from the high-voltage conversion unit 7, and generates a plurality of types of discharge products DP. In the generation unit 2, a high voltage obtained from the high-voltage conversion unit 7 is applied, which causes ionization to occur, and thus generates the plurality of types of discharge products DP such as ions D1 and ozone D2.

The generation unit 2 includes a discharge electrode 21. When a voltage is applied to a negative electrode of the generation unit 2, electrons are emitted from the discharge electrode 21. The electrons bond with oxygen or water present in the air in the vicinity of the discharge electrode 21, so that the discharge products DP are produced.

The electrons are emitted from the discharge electrode 21 more easily when an electric field is concentrated, compared to when the electric field is not concentrated. It is therefore desirable that the discharge electrode 21 is a needle electrode or other electrode made of conductive metal to concentrate the electric field. However, the discharge electrode 21 is not limited to the needle electrode, but may be an electrode with other shape, for example, a thin wire electrode or a brush electrode made of plural thin wires bundled together. The discharge electrode 21 is not limited to having the configuration described above. The discharge electrode 21 may be made up of a planar electrode and a linear electrode and have such a shape as to cause commonly-called creeping discharge.

The discharge electrode 21 is made of metal material. Note that the material of the discharge electrode 21 is not limited to metal, and the discharge electrode 21 may be made of other material, for example, conductive carbon fiber.

The generation unit 2 may include one discharge electrode 21, or may include a plurality of discharge electrodes 21. While the electrical polarity of voltage to be applied to the discharge electrode 21 is a negative polarity, the electrical polarity is not limited to the negative polarity, but may be a positive polarity. In a case where the generation unit 2 includes the plurality of discharge electrodes 21, the electrical polarity of voltage to be applied to the discharge electrodes 21 may differ between the discharge electrodes 21.

In a case where one discharge electrode 21 and one air-sending device 31 are provided, the control unit 5 can regulate the balance between the ions D1 and the ozone D2 by, for example, varying the voltage to be applied to the discharge electrode 21. The control unit 5 will be described later. The control unit 5 increases the voltage to be applied to the discharge electrode 21, and can accordingly improve the ratio of the ozone D2. In contrast, the control unit 5 decreases the voltage to be applied to the discharge electrode 21, and can accordingly improve the ratio of the ions D1. However, the absolute amount of the ions D1 decreases. Pulse application is effective to improve the ratio of the ions D1 while ensuring its absolute amount.

Figure 2:
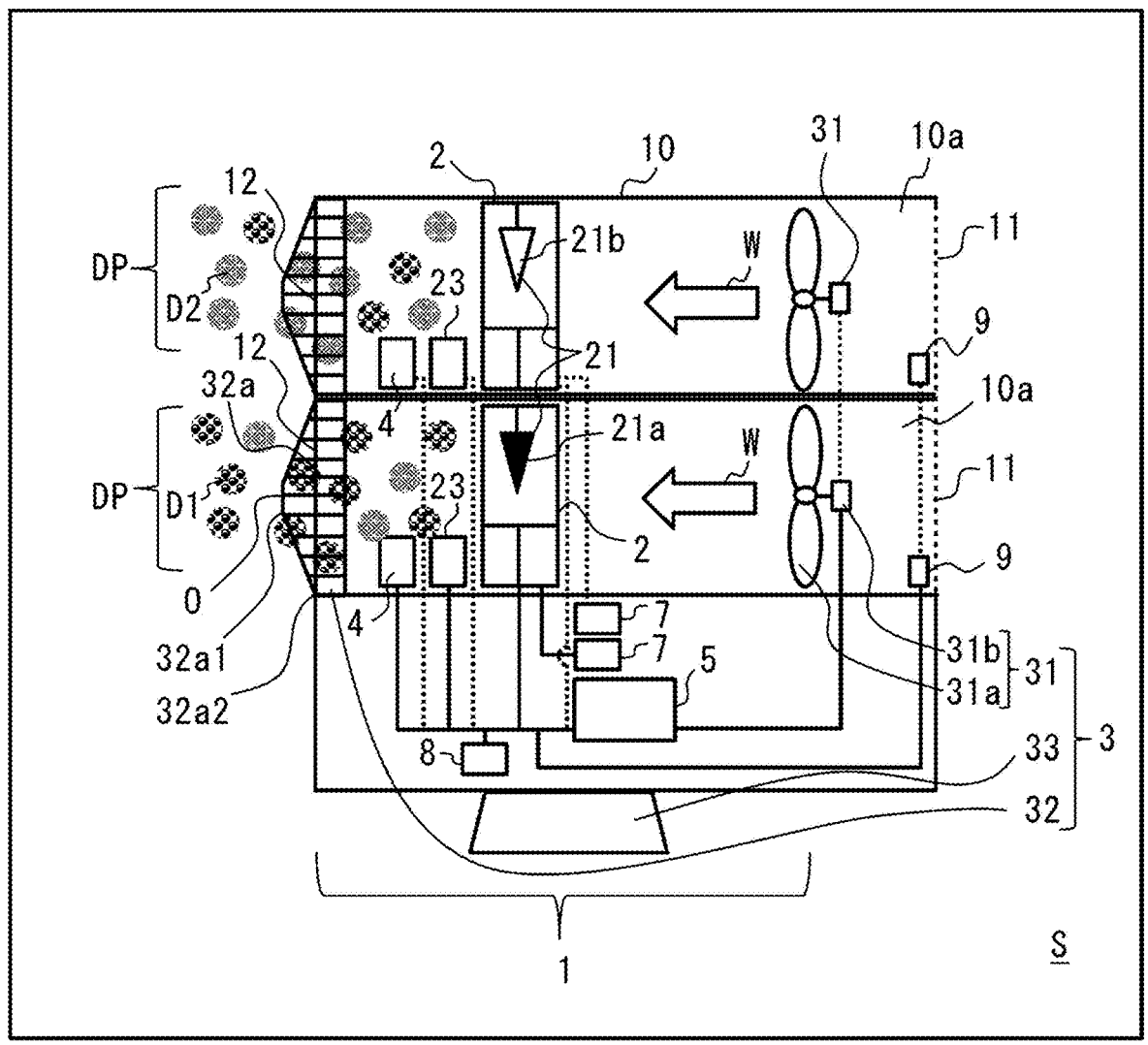
FIG. 2 is a schematic diagram illustrating another example of the relationship between the air cleaner according to Embodiment 1 and a space where the air cleaner is installed.

FIG. 2 is a schematic diagram illustrating another example of the relationship between the air cleaner 1 according to Embodiment 1 and the space S where the air cleaner 1 is installed. The generation unit 2 may be configured to vary the generation ratio between a plurality of types of discharge products DP by use of a plurality of discharge electrodes 21 with different configurations. For example, in the air cleaner 1, when a plurality of discharge electrodes 21 with different shapes are applied with an equal voltage, it is possible to emit the ions D1 and the ozone D2 whose respective amounts differ between the plurality of discharge electrodes 21 due to their different shapes. The air cleaner 1 varies the energization ratio between a discharge electrode 21a that is likely to emit the ions D1 and a discharge electrode 21b that is likely to emit the ozone D2, and can thereby change the generation ratio between the ions D1 and the ozone D2.

A single needle electrode is an example of the electrode that is likely to emit the ozone D2. For example, in a case where a voltage of 5 kV is applied to such an electrode as described above, the concentration of negative ions is 104 pieces/cc and the concentration of ozone is 0.024 ppm on a treatment target and its vicinity one meter away from the air cleaner 1 when there is a small amount of dust, while the concentration of negative ions is 101 pieces/cc and the concentration of ozone is 0.024 ppm on the treatment target and its vicinity one meter away from the air cleaner 1 when there is a large amount of dust.

A brush electrode made of plural fibers bundled together is an example of the electrode that is likely to emit the ions D1. In a case where a voltage of 5 kV is applied to such an electrode as described above, the concentration of negative ions is 105 pieces/cc and the concentration of ozone is 0.002 ppm on a treatment target and its vicinity one meter away from the air cleaner 1 when there is a small amount of dust, while the concentration of negative ions is 102 pieces/cc and the concentration of ozone is 0.002 ppm on the treatment target and its vicinity one meter away from the air cleaner 1 when there is a large amount of dust.

For example, when there is a small amount of dust, two electrodes that are likely to emit the ozone D2, and one electrode that is likely to emit the ions D1 are used, so that the concentration of negative ions is 105 pieces/cc and the concentration of ozone is 0.050 ppm. For another example, when there is a large amount of dust, one electrode that is likely to emit the ozone D2, and 10 electrodes that are likely to emit the ions D1 are used, so that the concentration of negative ions is $10^3$ pieces/cc and the concentration of ozone is 0.044 ppm. Such combined use of the electrodes as described above leads to a desirable balance between the ions D1 and the ozone D2.

FIG. 2 illustrates the configuration in which a generation unit 2 including the discharge electrode 21a, and a generation unit 2 including the discharge electrode 21b are located in separate air passages 10a. However, the generation unit 2 including the discharge electrode 21a, and the generation unit 2 including the discharge electrode 21b may be located together in the same air passage 10a. FIG. 2 also illustrates the configuration in which a single generation unit 2 including the discharge electrode 21a and a single generation unit 2 including the discharge electrode 21b are provided. However, the number of generation units 2 each including the discharge electrode 21a and the number of generation units 2 each including the discharge electrode 21b are not particularly limited. A plurality of generation units 2 each including the discharge electrode 21a may be provided and a plurality of generation units 2 each including the discharge electrode 21b may be provided.

The generation ratio between the ions D1 and the ozone D2 is not limited to a generation ratio controlled by use of the plurality of discharge electrodes 21 with different shapes. The control unit 5 in the air cleaner 1 can control the generation ratio between the ions D1 and the ozone D2 by, for example, changing the voltage to be applied to, or changing the pulse input frequency to, each of the plurality of discharge electrodes 21. The control unit 5 will be described later.

The discharge products DP act on, for example, microorganisms such as bacteria, and viruses adhering to the surfaces of furniture and fixtures such as a desk in a room, a wall, and a door knob, and inhibit growth of the microorganisms and viruses. The microorganisms such as bacteria are killed and their growth is inhibited by the discharge products DP. The viruses are inactivated by the discharge products DP.

Examples of the discharge products DP include the ions D1 and the ozone D2. The ions D1 are, for example, negative ions. It is desirable to maintain the balance between ion concentration and ozone concentration in a manner as described below, in order that the discharge products DP act on the microorganisms and viruses adhering to the aforementioned surfaces of the treatment target to inhibit growth of the microorganisms or to help inactivate the viruses. It is desirable to maintain such a balance that when the ozone concentration is 0.05 ppm, which is defined as the environmental standards, the ion concentration is $10^3$ to $10^8$ pieces/cc. The generation unit 2 supplies the discharge products DP with the concentrations and the balance being maintained as described above, so that it is effective to prevent growth of various microorganisms and viruses. Even in a concentration region where it is impossible to inhibit the growth of microorganisms and viruses by only use of either the ions D1 or the ozone D2, the synergy effect of the ions D1 and the ozone D2 makes it possible to inhibit the growth of microorganisms and viruses.

In an air cleaner using the discharge products DP, the amount of discharge products, and the balance between the elements that make up the discharge products are also important for the air cleaner to exhibit adequate sterilization performance and inactivation performance. Contact of the discharge products DP emitted to the space with dust causes a reduction of the discharge products DP present in the space. This prevents the amount of discharge products DP present in the space, and the balance between the elements that make up the discharge products DP from both being maintained, which causes a concern about degradation in the sterilization performance and inactivation performance.

Specifically, in a case where the discharge products DP are the ions D1 and the ozone D2, the ions D1 bond with dust in the air and the amount of the ions D1 decreases accordingly, while the amount of the ozone D2 is unlikely to decrease despite bonding with the dust. For this reason, when the ions D1 and the ozone D2 are emitted whose respective amounts are the same between both cases when there is a large amount of dust and when there is a small amount of dust, the ratio between the ions D1 and the ozone D2 at the point in time when they reach the treatment target, that is, the balance between the ions D1 the ozone D2 differs between the both cases. Therefore, even when the discharge products DP are emitted to the treatment target in consideration of the balance between the ions D1 and the ozone D2, depending on the amount of dust, the discharge products DP that reach the treatment target may not maintain the balance between the ions D1 and the ozone D2.

The control unit 5 has, for example, a predetermined reference amount of dust to be used as a reference, and determines the emission amounts of the ions D1 and the ozone D2 based on the reference amount of dust. The control unit 5 will be described later. When the amount of dust floating in the space S is "larger" than the reference amount of dust, the control unit 5 determines that a decreased amount of the ions D1 is emitted. In contrast, when the amount of dust floating in the space S is "smaller" than the reference amount of dust, the control unit 5 determines that the amount of the ions D1 to be emitted is unlikely to decrease and an excessive amount of the ions D1 is supplied.

For example, when there is a "large" amount of dust floating in the space S and the control unit 5 thus determines that a decreased amount of the ions D1 is emitted, then the control unit 5 controls the devices such as the generation unit 2 and the air-sending device 31 in such a manner as to generate an increased amount of the ions D1 relative to a specified amount of the ions D1 that is predetermined for the treatment target. For another example, when there is a "small" amount of dust floating in the space S and the control unit 5 thus determines that an excessive amount of the ions D1 is emitted, then the control unit 5 controls the devices such as the generation unit 2 and the air-sending device 31 in such a manner as to generate a decreased amount of the ions D1 relative to the specified amount of the ions D1 that is predetermined for the treatment target.

The air cleaner 1 may be provided with the measurement unit 23 configured to measure the amount of the discharge products DP to check for the concentration of the discharge products DP, and the balance between the elements that make up the discharge products DP such as the ions D1 and the ozone D2. The measurement unit 23 can detect chemical species that make up the discharge products DP emitted by electric discharge, and measure the concentration of the chemical species. The measurement unit 23 is, for example, an ion sensor that can detect the presence of the ions D1 and measure their concentration. Note that the ion sensor is merely an example, and the measurement unit 23 is not limited to the ion sensor, but may be other type of sensor as long as the sensor can detect chemical species emitted by electric discharge and the concentration of the chemical species. The measurement unit 23 such as an ion sensor is located downstream of the generation unit 2 in an air-sending direction W along which a flow of air is formed by the air-sending unit 3.

In a case where the measurement unit 23 is an ion sensor, the measurement unit 23 is, for example, a coaxial double-cylinder sensor configured to detect the presence of plus ions or minus ions in the air to be supplied by the air-sending unit 3 and measure their concentration. This allows the air cleaner 1 to detect the presence of plus ions and the presence of minus ions and measure their concentration simultaneously by use of the same sensor, and to detect their presences and measure their concentration in a wide area with high accuracy.

The control unit 5 compares an ion detection amount detected by the measurement unit 23 serving as an ion sensor with a preset target value of ions to be supplied, and controls the generation unit 2 based on a result of the comparison. The control unit 5 will be described later. The control unit 5 controls the generation unit 2 in this manner, so that the amount of ions to be supplied to an object on which microorganisms and viruses grow, or to the space S that is an air-conditioning target space can be maintained at a fixed amount. The air cleaner 1 can thus minimize as possible the growth of microorganisms and viruses, and inhibit the growth of microorganisms and viruses.

(Air-Sending Unit 3)

The air-sending unit 3 forms a flow of air to generate wind. The air-sending unit 3 sprays a plurality of types of discharge products DP generated from the generation unit 2 to the space S. The air-sending unit 3 is provided in the vicinity of the generation unit 2. The discharge products DP generated from the generation unit 2 reach the surfaces of furniture and fixtures such as a desk in a room, by use of the wind formed by the air-sending unit 3, and act on microorganisms adhering to these surfaces.

The air-sending unit 3 includes the air-sending device 31 configured to generate an airflow, a grille 32 configured to improve the directionality and straightness of the airflow, and a drive device 33 configured to drive the casing 10 such that the generated airflow blows out toward the treatment target that is targeted for sterilization of the microorganisms and inactivation of the viruses. Note that it suffices that the air-sending unit 3 includes at least the air-sending device 31 configured to generate an airflow, and it is allowable that the air-sending unit 3 is made up of only the air-sending device 31.

The air-sending device 31 configured to generate an airflow, and the grille 32 configured to improve the directionality and straightness of the airflow are provided in the air passage 10a formed in the casing 10. The grille 32 is located on the exit side of the air passage 10a. An air-sending fan 31a is supported on an inner wall of the casing 10 such that the air-sending fan 31a is positioned at the center axis of the air passage 10a.

The air-sending device 31 includes the air-sending fan 31a and a motor 31b configured to drive the air-sending fan 31a. When the air-sending fan 31a is driven, the ambient air around the casing 10 is sucked into the casing 10 from an air inlet 11. At an entrance of the air passage 10a, the sucked air changes its flow direction from the radial direction to the axial direction. Wind delivered by the air-sending device 31 is blown out from the casing 10 from an exit of the air passage 10a through the grille 32.

The air-sending fan 31a is, for example, an axial-flow propeller fan. The axial-flow propeller fan is employed as the air-sending fan 31a, so that the air-sending fan 31a can generate a large volume of airflow. While the motor 31b connected to the air-sending fan 31a is a general AC capacitor motor, the motor 31b is not limited to the AC capacitor motor.

When the grille 32 is viewed in the air-sending direction W in which wind is delivered from the air-sending device 31, fins 32a are provided in a spiral form. The grille 32 includes the fins 32a in a spiral form. A plurality of fins 32a are provided between the central side and the outer peripheral side of the grille 32.

In the grille 32, an inner end portion 32a1 of the plurality of fins 32a protrudes in the air-sending direction W relative to an outer end portion 32a2 of the plurality of fins 32a. The inner end portion 32a1 is closer to a center O of the spiral than is the outer end portion 32a2. The outer end portion 32a2 continues into an air outlet 12 of the casing 10. In other words, relative to the outer end portion 32a2 of a portion of the grille 32 where the plurality of fins 32a are formed, the inner end portion 32a1 protrudes in the air-sending direction W. The inner end portion 32a1 is an inner-end side portion of the fins 32a located closer to the center O of the spiral than is the outer end portion 32a2, and includes a portion in the vicinity of the inner end. The outer end portion 32a2 is an outer-end side portion that continues into the air outlet 12.

The air-sending unit 3 includes the grille 32 of the structure described above, so that wind gathers at the center and converges, and can thereby increase the wind speed at the center in the air-sending direction W. The wind to be blown out from the air outlet 12 of the casing 10 becomes a spiral airflow that can extend the reaching distance of the wind, so that the air-sending unit 3 can form an airflow with improved directionality and straightness.

The drive device 33 drives the casing 10 such that an airflow generated by the air-sending device 31 blows out toward the treatment target that is targeted for sterilization of the microorganisms and inactivation of the viruses, to change the air-sending direction. The drive device 33 changes the orientation of the casing 10 such that the exit of the air passage 10a of the casing 10 can be directed toward the entirety of the furniture and fixtures present in the space S.

Specifically, the drive device 33 includes a motor (not illustrated) that can drive to two axes perpendicular to each other. The motor is a general servo motor or stepping motor. These motors can control the angle of a shaft supporting the casing 10, and also stop the shaft supporting the casing 10 at a certain position, and can thus direct the exit of the air passage 10a toward the treatment target that is targeted for sterilization of the microorganisms and inactivation of the viruses and then stop the exit accurately in the space S.

A main substrate (not illustrated) is provided on a side wall of the air passage 10a of the casing 10. On the main substrate, a controller made up of a central processing unit (CPU) and other units, a power supply device configured to supply power to the units, and other devices are mounted.

Note that the air-sending unit 3 may include a plurality of air-sending devices 31 as illustrated in FIG. 2. In the air cleaner 1, the plurality of air-sending devices 31 may be individually located for the respective discharge electrodes 21. In this case, the control unit 5 may control the plurality of air-sending devices 31 to change their respective air-sending volumes in response to a voltage application control exercised by the control unit 5. A case may be considered where each of the plurality of discharge electrodes 21 may have different characteristics, for example, a case where the generation unit 2 includes a discharge electrode 21 from which a large amount of the ozone D2 is generated and a discharge electrode 21 from which a large amount of the ions D1 is generated. In this case, by use of different air-sending volumes to the discharge electrodes 21, the control unit 5 can easily control the balance between the elements that make up the discharge products DP in the space S.

(Estimation Unit 4)

The estimation unit 4 estimates the amount of dust floating in the space S where the air cleaner 1 is installed. For example, the estimation unit 4 estimates the amount of dust floating in the space S by selecting whether the amount of dust floating in the space is a first estimation amount smaller than a predetermined threshold or is a second estimation amount larger than or equal to the predetermined threshold and larger than the first estimation amount. That is, the estimation unit 4 determines whether there is a large or small amount of dust floating in the space S. As an example, the amount of dust is determined by use of two levels "larger" and "smaller" compared to a preset threshold. In this case, the amount of dust "smaller" than the threshold is determined as the first estimation amount, while the amount of dust larger than or equal to the threshold is determined as the second estimation amount.

Note that the determination of the amount of dust is not limited to use of the two levels. The amount of dust may be determined by use of three levels, "larger," "normal," and "smaller" compared to the preset threshold. The amount of dust may be determined by use of criteria with more than three levels to be compared to the preset threshold. The estimation unit 4 performs a multiple-level determination, so that it is possible to finely specify control notches for the air volume to be delivered by the air-sending device 31 and the amount of the discharge products DP to be emitted by the generation unit 2, and it is thus possible to properly control generation of the discharge products DP according to the amount of dust.

When determining the amount of dust floating in the space S by use of three levels, the estimation unit 4 estimates, at the first stage, for example whether the amount of dust floating in the space S is categorized as the first estimation amount or the second estimation amount. When determining that the amount of dust floating in the space S is categorized as the second estimation amount, the estimation unit 4 determines that there is a "large" amount of dust floating in the space S.

When determining that the amount of dust floating in the space S is categorized as the first estimation amount, the estimation unit 4 further estimates, at the second stage, whether the amount of dust floating in the space S is categorized as a third estimation amount or a fourth estimation amount. The third estimation amount for the amount of dust floating in the space S is smaller than a predetermined second threshold. The fourth estimation amount for the amount of dust floating in the space S is larger than or equal to the predetermined second threshold. The second threshold is a value smaller than the first threshold. The third estimation amount is smaller than the fourth estimation amount. When determining that the amount of dust floating in the space S is categorized as the third estimation amount, the estimation unit 4 determines that there is a "small" amount of dust floating in the space S. When determining that the amount of dust floating in the space S is categorized as the fourth estimation amount, the estimation unit 4 determines that there is a "normal" amount of dust floating in the space S.

The air cleaner 1 includes a dust sensor 9 that serves as a detection unit to estimate the amount of dust. The dust sensor 9 is configured to measure the amount of dust in the space S. The dust sensor 9 is connected to the estimation unit 4 and the control unit 5 with a wire or wirelessly. The estimation unit 4 estimates the amount of dust in the space S based on the amount of dust measured by the dust sensor 9. The estimation unit 4 has a threshold that is preset according to the amount of dust, and determines the amount of dust based on a comparison between a signal transmitted from the dust sensor 9 and the preset threshold.

The estimation unit 4 has the preset threshold stored in the estimation unit 4. The estimation unit 4 compares information on the amount of dust input from the dust sensor 9 through a communication module or other device with the stored threshold to determine whether there is a large or small amount of dust. The air cleaner 1 improves the accuracy in determining the amount of dust by combining a plurality of determination means configured to determine the amount of dust.

The estimation unit 4 is provided with an operating-status determination unit (not illustrated). The operating-status determination unit in the estimation unit 4 receives an input of signals indicating the operating status and operating mode of the air cleaner itself. The method for estimating the amount of dust is not limited to estimation based on a comparison between the amount of dust measured by the dust sensor 9 and the preset threshold. For example, the estimation unit 4 may estimate the amount of dust in the space S based on the operating condition of the air cleaner 1 itself.

Specifically, in a case where the air cleaner 1 includes a heat exchanger 71 (see FIG. 3) and serves as an air-conditioning apparatus 70 (see FIG. 3), when the temperature regulating function is enabled, the air passing through the heat exchanger 71 blows into the room. Consequently, dust is likely to fly up from the floor or other location. For this reason, in a case where the air cleaner 1 includes the heat exchanger 71, when the temperature regulating function is enabled, the estimation unit 4 determines that the amount of dust in the space S is the second estimation amount and thus there is a "large" amount of dust. In a case where the air cleaner 1 includes the heat exchanger 71, when the temperature regulating function is not enabled, dust is unlikely to fly up from the floor or other location. For this reason, in a case where the air cleaner 1 includes the heat exchanger 71, when the temperature regulating function is not enabled, the estimation unit 4 determines that the amount of dust in the space S is the first estimation amount and thus there is a "normal" or "small" amount of dust.

Figure 3:
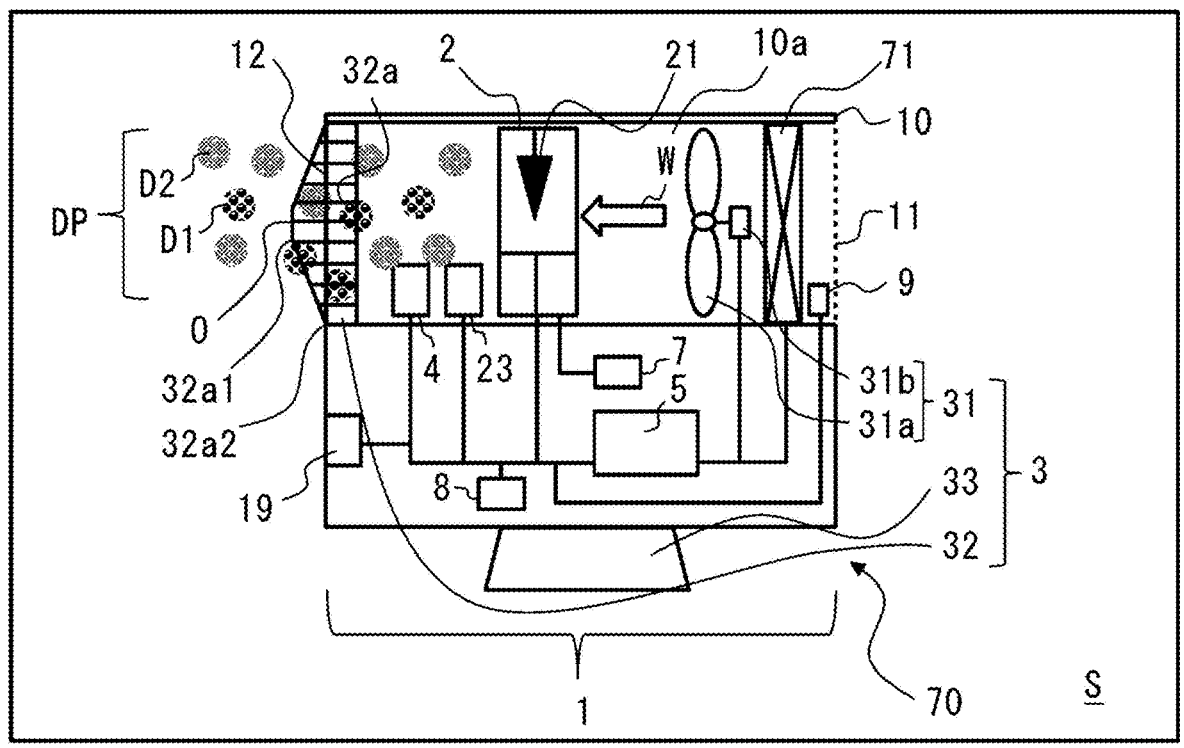
FIG. 3 is a schematic diagram illustrating an example of an air-conditioning apparatus including the air cleaner according to Embodiment 1.

FIG. 3 is a schematic diagram illustrating an example of the air-conditioning apparatus 70 including the air cleaner 1 according to Embodiment 1. With reference to FIG. 3, the above case where the air cleaner 1 includes the heat exchanger 71 and serves as the air-conditioning apparatus 70 is explained below.

The air-conditioning apparatus 70 includes the air cleaner 1 and the heat exchanger 71 configured to exchange heat between refrigerant flowing inside the heat exchanger 71 and air that is present around the heat exchanger 71. In the air-conditioning apparatus 70, air supplied by the air-sending unit 3 passes through the heat exchanger 71. The air-conditioning apparatus 70 supplies a plurality of types of the discharge products DP to the space S, by use of conditioned air passing through the heat exchanger 71. Note that, in FIG. 3, the heat exchanger 71 is located upstream of the air-sending device 31 in the air-sending direction W, the heat exchanger 71 may be located downstream of the air-sending device 31.

The method for estimating the amount of dust is not limited to the estimation based on the amount of dust measured by the dust sensor 9, or the estimation based on the operating condition of the air cleaner itself as described above. For example, the air cleaner 1 may include a human-presence sensor 19. The human-presence sensor 19 detects whether a person is present in the space S. The estimation unit 4 estimates the amount of dust in the space S based on the detection of whether a person is present by the human-presence sensor 19.

More specifically, the estimation unit 4 determines whether a person is present in the room based on a signal transmitted from the human-presence sensor 19 on the basis of detection by the human-presence sensor 19. When a person is present in the room, the estimation unit 4 determines that a person is active in the room, the amount of dust in the space S is the second estimation amount, and thus there is a "large" amount of dust. In a case where the air cleaner 1 includes the human-presence sensor 19, when the estimation unit 4 determines that a person is not present in the room based on the detection by the human-presence sensor 19, the estimation unit 4 determines that a person is not active in the room, the amount of dust in the space S is the first estimation amount, and thus there is a "normal" or "small" amount of dust.

Furthermore, the estimation unit 4 may receive information transmitted not only from the air cleaner itself, but also from other devices that are present in the space S where the air cleaner 1 is located, and thus determine the amount of dust in the space S.

Figure 4:
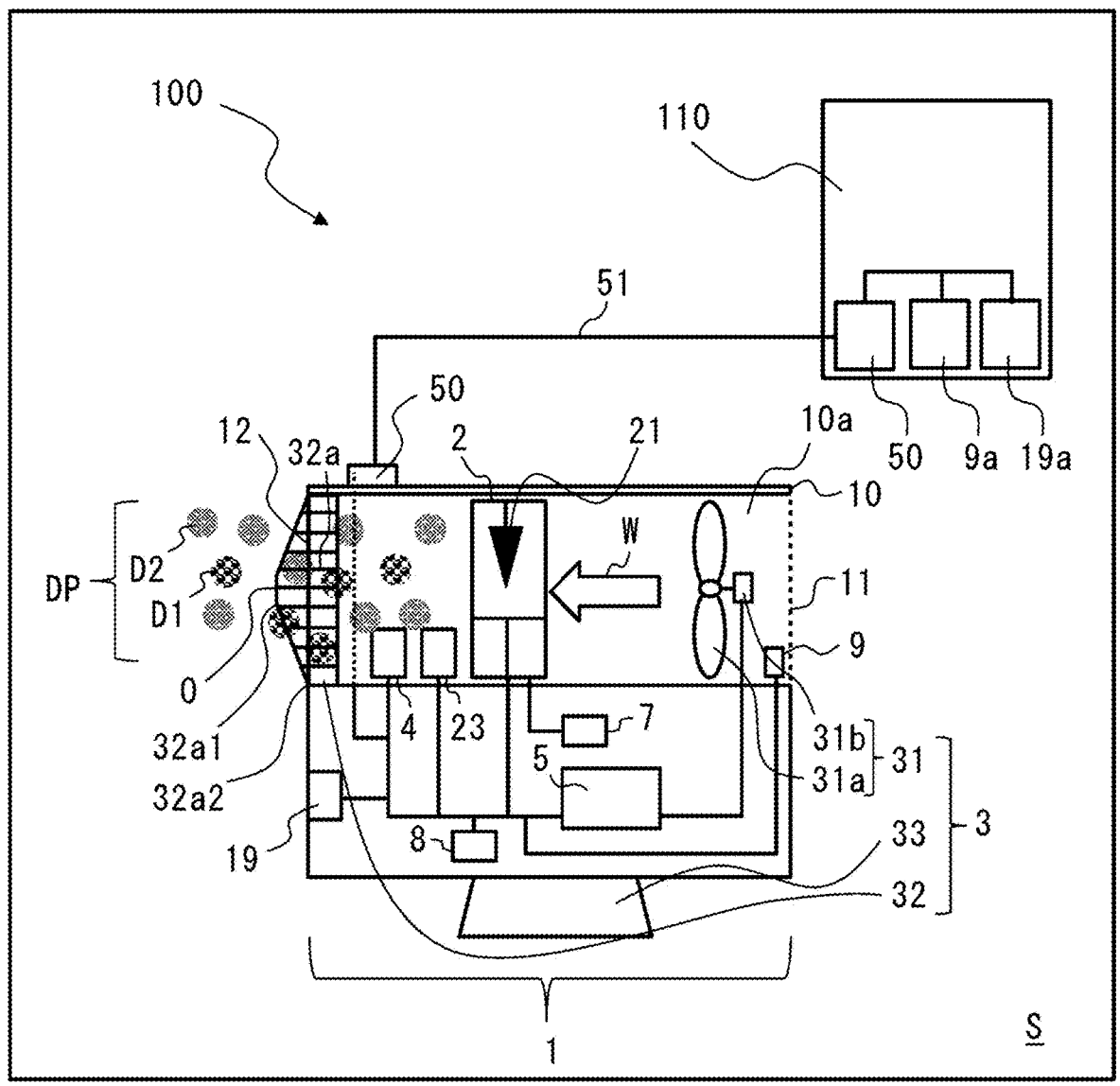
FIG. 4 is a schematic diagram illustrating an example of an air cleaner system including the air cleaner according to Embodiment 1.

FIG. 4 is a schematic diagram illustrating an example of an air cleaner system 100 including the air cleaner 1 according to Embodiment 1. The air cleaner system 100 includes the air cleaner 1, and an additional device 110 located in the space S where the air cleaner 1 is located.

The air cleaner 1 and the additional device 110 include respective communication modules 50 as an information transmission means through which they are allowed to communicate with each other. For example, a communication harness 51 is connected between the communication module 50 of the air cleaner itself and the communication module 50 of the additional device 110. The air cleaner itself and the additional device 110 are connected to each other by use of the communication harness 51. Note that examples of the additional device 110 include an additional air cleaner 1 separate from the air cleaner 1 located in the space S, an air-conditioning apparatus, a lighting device, and a room-entry management system, however, the additional device 110 is not limited to these devices. These devices will be described later.

The operating-status determination unit in the estimation unit 4 receives an input of information on the operating status of the additional device 110 from this additional device 110 via the communication harness 51. Note that in a case where the air cleaner itself is distanced from the additional device 110, wireless communication may be used for connection between the communication modules 50 without via the communication harness 51 as an information transmission means between the air cleaner itself and the additional device 110. The air cleaner itself and the additional device 110 include respective communication modules 50, and are connected to each other through wireless communication. The air cleaner system 100 performs wireless communication by use of the communication module 50 of the air cleaner itself and the communication module 50 of the additional device 110. The estimation unit 4 in the air cleaner 1 receives an input of information on the operating status and other conditions of the additional device 110.

The additional device 110 further includes a second dust sensor 9a configured to measure the amount of dust in the space S. The estimation unit 4 in the air cleaner 1 receives information on the amount of dust detected by the second dust sensor 9a mounted on the additional device 110 located in the space S. The estimation unit 4 in the air cleaner 1 receives the information on the amount of dust measured by the second dust sensor 9a through the communication modules 50 and estimates the amount of dust in the space S.

Alternatively, the additional device 110 further includes a second human-presence sensor 19a configured to measure the amount of dust in the space S. The estimation unit 4 in the air cleaner 1 receives information detected by the second human-presence sensor 19a mounted on the additional device 110 located in the space S. The estimation unit 4 in the air cleaner 1 estimates the amount of dust in the space S based on the detection of whether a person is present by the second human-presence sensor 19a.

Alternatively, the estimation unit 4 in the air cleaner 1 estimates the amount of dust in the space S based on information on the operating condition of the additional device 110 received through the communication modules 50.

In a case where the additional device 110 is an air-conditioning apparatus, when the air cleaner itself receives information indicating that the air-conditioning apparatus regulates the temperature or delivers air, the estimation unit 4 determines that a person is active in the room, the amount of dust in the space S is the second estimation amount, and thus there is a "large" amount of dust. In a case where the additional device 110 is an air-conditioning apparatus, when the air cleaner itself receives information indicating that the air-conditioning apparatus does not regulate the temperature and does not deliver air, the estimation unit 4 determines that a person is not active in the room, the amount of dust in the space S is the first estimation amount, and thus there is a "normal" or "small" amount of dust. In a case where the additional device 110 is an air-conditioning apparatus, when the air cleaner itself does not receive information indicating that the air-conditioning apparatus regulates the temperature or delivers air, the estimation unit 4 determines that a person is not active in the room, the amount of dust in the space S is the first estimation amount, and thus there is a "normal" or "small" amount of dust.

In a case where the additional device 110 is a lighting device, when the air cleaner itself receives information indicating that the lighting device is lit, the estimation unit 4 determines that a person is active in the room, the amount of dust in the space S is the second estimation amount, and thus there is a "large" amount of dust. In a case where the additional device 110 is a lighting device, when the air cleaner itself receives information indicating that the lighting device is unlit, the estimation unit 4 determines that a person is not active in the room, the amount of dust in the space S is the first estimation amount, and thus there is a "normal" or "small" amount of dust. In a case where the additional device 110 is a lighting device, when the air cleaner itself does not receive information indicating that the lighting device is lit, the estimation unit 4 determines that a person is not active in the room, the amount of dust in the space S is the first estimation amount, and thus there is a "normal" or "small" amount of dust.

In a case where the additional device 110 is a room-entry management system, when the air cleaner itself receives information based on the room-entry management system and indicating, for example, the presence or absence of a person in the room, the estimation unit 4 determines that a person is active in the room when the information indicates that a person is present in the room, and then determines that the amount of dust in the space S is the second estimation amount and thus there is a "large" amount of dust. In a case where the additional device 110 is a room-entry management system, when the air cleaner itself receives information based on the room-entry management system and indicating, for example, the presence or absence of a person in the room, the estimation unit 4 determines that a person is not active in the room when the information indicates that a person is absent in the room, and then determines that the amount of dust in the space S is the first estimation amount and thus there is a "normal" or "small" amount of dust.

With reference back to FIG. 1, the air cleaner 1 may include a time measuring unit 8. The time measuring unit 8 is connected to the estimation unit 4 and the control unit 5. The time measuring unit 8 may be included in the estimation unit 4 or the control unit 5, or may be included in both the estimation unit 4 and the control unit 5. The time measuring unit 8 includes, for example, a timer and a real-time clock. The time measuring unit 8 is used to obtain the current time and measure a set time.

After having determined that there is a "large" amount of dust based on the information on the air cleaner itself or the additional device 110, when the estimation unit 4 detects, for example, that operation of the air cleaner itself or the additional device 110 stops, or detects that a person has left the room, the estimation unit 4 determines that there is a "normal" amount of dust within 30 minutes after the detection. Subsequently, after 30 minutes have elapsed since the detection of the stop of operation or other behavior, the estimation unit 4 determines that there is a "small" amount of dust. Note that "30 minutes" is a period of time required for 5 μm-particles to settle down.

(Control Unit 5)

The control unit 5 controls operation of the air cleaner 1 based on the amount of dust in the space S estimated by the estimation unit 4. The control unit 5 controls the generation amount of a plurality of types of the discharge products DP to be generated from the generation unit 2 based on the amount of dust estimated by the estimation unit 4. The control unit 5 can further control the generation ratios of respective discharge products that make up the plurality of types of the discharge products DP. The control unit 5 regulates the voltage to be applied to the generation unit 2, and regulates the air volume of the air-sending device 31 as needed. A result of determination performed by the estimation unit 4 is input to the control unit 5 through a harness. The control unit 5 is connected to the generation unit 2 and the air-sending unit 3 through harnesses, and transmits a control signal to these units.

When the estimation unit 4 determines that there is a "small" amount of dust in the space S, the control unit 5 causes the generation unit 2 to generate a predetermined normal amount of the discharge products DP to be emitted. When the estimation unit 4 determines that there is a "normal" amount of dust in the space S, the control unit 5 controls the generation unit 2 in such a manner as to increase the generation ratio of a discharge product DP whose amount is likely to be decreased by the dust, and thereby regulates the generation amount of the discharge products DP. When the estimation unit 4 determines that there is a "large" amount of dust in the space S, the control unit 5 controls the generation unit 2 to stop generation of the discharge products DP.

The generation amount of the discharge products DP is regulated by regulating the amount of electric discharge. For example, the control unit 5 regulates the voltage to be applied to the discharge electrode 21 of the generation unit 2, thereby to regulate the amount of the discharge products DP to be generated. Note that regulation of the generation amount of the discharge products DP is not limited to regulation of the voltage to be applied to the generation unit 2. For example, regulation of the generation amount of the discharge products DP may be performed by regulating the frequency at which power is supplied to the generation unit 2. For another example, regulation of the generation amount of the discharge products DP may be performed by switching on and off of the voltage application to a plurality of discharge electrodes 21 with different characteristics. The control exercised in this manner can prevent, by association of floating dust with some of the discharge products DP, the discharge products DP from being unnecessarily consumed, so that the air cleaner 1 can efficiently generate the discharge products DP.

Next, an example of the control to be exercised by the control unit 5 in a case where the air cleaner 1 includes a plurality of generation units 2 is described with reference to FIG. 2. As illustrated in FIG. 2, the air cleaner 1 includes a plurality of generation units 2 with different characteristics of generation of the discharge products DP, and a plurality of air-sending devices 31 provided corresponding to the plurality of respective generation units 2 and capable of delivering different volumes of air to the plurality of respective generation units 2. The control unit 5 varies the generation amount of the discharge products DP to be emitted to the exterior of the device by use of different volumes of air to be delivered to the plurality of respective generation units 2 according to the amount of dust estimated by the estimation unit 4. Note that the plurality of generation units 2 with different characteristics of generation of the discharge products DP include, for example, a generation unit 2 provided with the discharge electrode 21a from which a high ratio of the ions D1 is generated, and a generation unit 2 provided with the discharge electrode 21b from which a high ratio of the ozone D2 is generated.

More specifically, when the estimation unit 4 determines that there is a "large" amount of dust, the amount of the ozone D2 still remains unchanged at the time when the ozone D2 reaches the target. However, because the ions D1 are likely to bond with the dust and thus the amount of the ions D1 is likely to decrease, the control unit 5 needs to increase the amount of the ions D1 to be generated relative to the amount of the ions D1 to be generated when the amount of dust is determined as "normal" or "small" to compensate for the decreased amount of the ions D1. For this reason, the control unit 5 controls and increases the amount of the ions D1 to be generated relative to the amount of the ions D1 to be generated when there is a "normal" or "small" amount of dust.

As illustrated in FIG. 2, the air-sending devices 31 are installed corresponding to the plurality of discharge electrodes 21. The air volume of the air-sending device 31 that pairs up with the discharge electrode 21b, from which a high ratio of the ozone D2 is generated, remains unchanged from the air volume when there is a "normal" or "small" amount of dust. In contrast, the control unit 5 increases the air volume of the air-sending device 31 that pairs up with the discharge electrode 21a, from which a high ratio of the ions D1 is generated, relative to the air volume when there is a "normal" or "small" amount of dust, thereby to increase the amount of the ions D1 to be generated in the generation unit 2.

When the estimation unit 4 determines that there is a "small" amount of dust, the amount of the ozone D2 still remains unchanged at the time when the ozone D2 reaches the target. There is a small amount of dust and thus the amount of the ions D1 is unlikely to decrease. Consequently, when a specified amount of the ions D1 that is predetermined for the treatment target is generated, an excessive amount of the ions D1 is supplied. For this reason, the control unit 5 needs to decrease the amount of the ions D1 to be generated relative to the amount of the ions D1 to be generated when there is a "normal" or "large" amount of dust. The control unit 5 thus controls and decreases the amount of the ions D1 to be generated relative to the amount of the ions D1 to be generated when there is a "normal" or "large" amount of dust.

As illustrated in FIG. 2, the air-sending devices 31 are installed corresponding to the plurality of discharge electrodes 21. The air volume of the air-sending device 31 that pairs up with the discharge electrode 21b, from which a high ratio of the ozone D2 is generated, remains unchanged from the air volume when there is a "normal" or "large" amount of dust. In contrast, the control unit 5 decreases the air volume of the air-sending device 31 that pairs up with the discharge electrode 21a, from which a high ratio of the ions D1 is generated, relative to the air volume when there is a "normal" or "large" amount of dust, thereby to decrease the amount of the ions D1 to be generated in the generation unit 2.

(High-Voltage Conversion Unit 7)

The high-voltage conversion unit 7 converts a voltage input to the air cleaner 1 to a high voltage. The high-voltage conversion unit 7 is a commonly-called boosting transformer that is a piezoelectric transformer-system high-voltage generator configured to boost an input voltage through a piezoelectric transformer in a high-voltage generation circuit.

It is desirable that the high-voltage conversion unit 7 employs the piezoelectric transformer system, taking into account the benefits such as noise reduction. Note that the high-voltage conversion unit 7 is not limited to the piezoelectric transformer-system high-voltage generator, and a winding transformer-system high-voltage generator may also be used as the high-voltage conversion unit 7. The voltage boosted to several kilovolts by the high-voltage conversion unit 7 is applied to the generation unit 2.

Figure 5:
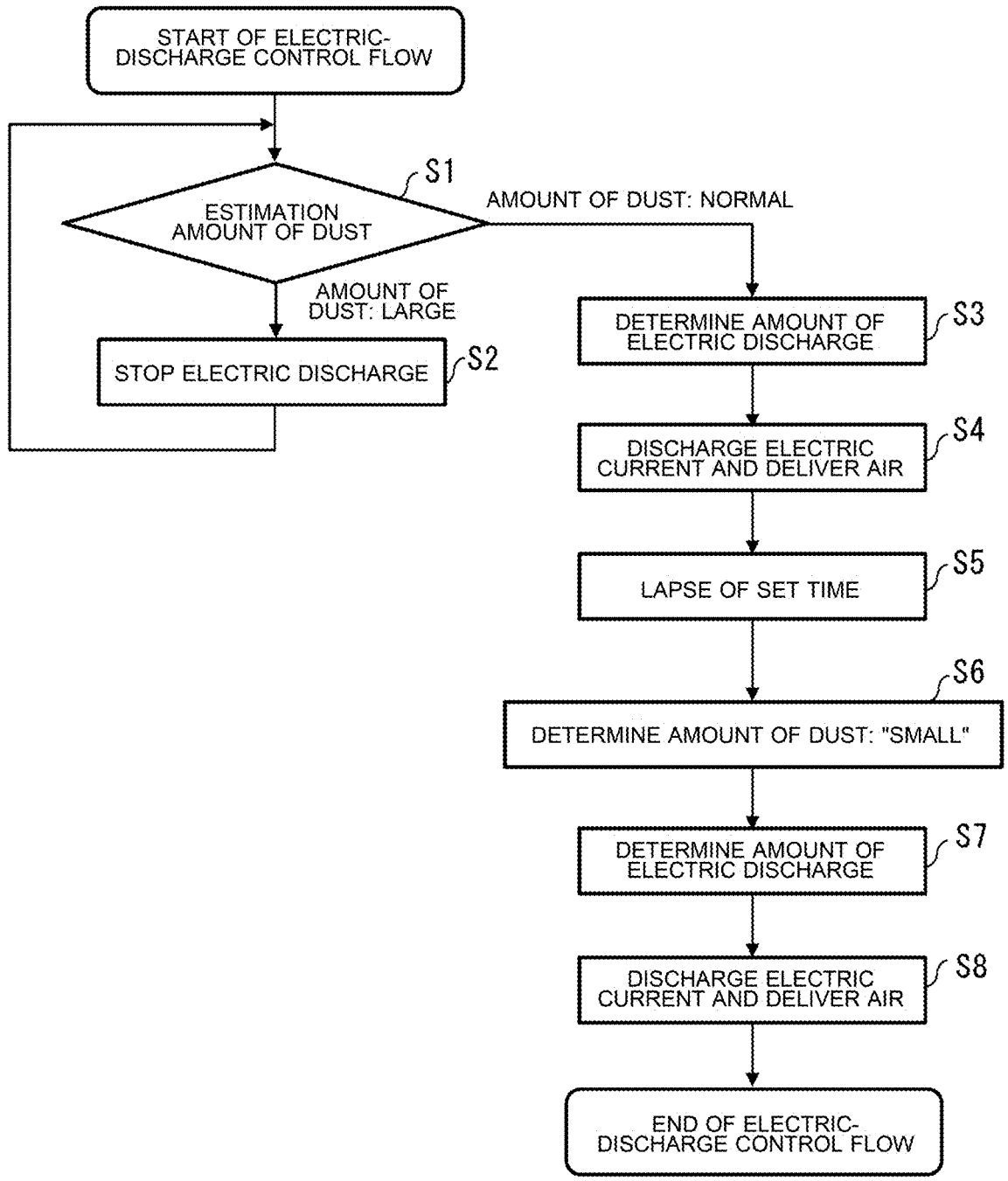
FIG. 5 is a flowchart illustrating operation of the air cleaner according to Embodiment 1.

FIG. 5 is a flowchart illustrating operation of the air cleaner 1 according to Embodiment 1. The control unit 5 in the air cleaner 1 according to Embodiment 1 controls generation of the discharge products DP according to the amount of dust in the space S as described above. With reference to FIG. 5, an example of the control is described below in which the control unit 5 controls generation of the discharge products DP according to the amount of dust in the space S.

When an electric-discharge control flow starts, the estimation unit 4 estimates the amount of dust in the space S where the air cleaner 1 is installed (step S1). As described above, the amount of dust may be estimated by comparing the amount of dust measured by the dust sensor 9 with the predetermined threshold, or may be estimated based on the operating condition of the air cleaner itself or the additional device 110.

For example, the electric-discharge control flow starts when the air cleaner 1 starts up. Note that the timing at which the electric-discharge control flow starts is not limited to the start-up of the air cleaner 1. For example, the air cleaner 1 may start the electric-discharge control flow when a user issues a command to start the electric-discharge control flow by pressing a switch during operation of the air cleaner 1. For another example, the air cleaner 1 may start the electric-discharge control flow at a predetermined certain time. The air cleaner 1 may start the electric-discharge control flow, for example, on an hourly basis or at predetermined time intervals.

In step S1, when the estimation unit 4 determines that the amount of dust in the space S is the second estimation amount, and thus there is a "large" amount of dust in the space S, then the control unit 5 controls the generation unit 2 to stop electric discharge (step S2). Electric discharge is stopped in the generation unit 2, and thus emission of the discharge products DP from the generation unit 2 is stopped. Note that when the generation unit 2 is in a state of stopping electric discharge, for example, at the start-up of the air cleaner 1, this state is maintained. When the air cleaner 1 is in operation, electric discharge from the generation unit 2 is stopped.

In step S2, when the air-sending device 31 is in a state of stopping operation, for example, at the start-up of the air cleaner 1, this state is maintained. In step S2, when the air cleaner 1 is in operation, the control unit 5 controls the air-sending device 31 and stops operation of the air-sending device 31.

In step S1, when the estimation unit 4 determines that the amount of dust in the space S is the first estimation amount, and thereafter determines that the amount of dust in the space S is the fourth estimation amount, and thus there is a "normal" amount of dust in the space S, then the control unit 5 determines the amount of electric discharge by the generation unit 2 (step S3). The amount of electric discharge to be determined in step S3 is predetermined as a first amount of electric discharge when there is a "normal" amount of dust. In step S3, when the control unit 5 determines the amount of electric discharge by the generation unit 2, the control unit 5 controls the generation unit 2 such that the generation unit 2 discharges an electric current based on the determined amount of electric discharge (step S4).

Note that when the generation unit 2 is in a state of stopping electric discharge, for example, at the start-up of the air cleaner 1, then the generation unit 2 starts electric discharge based on the determined amount of electric discharge and discharges an electric current. When the air cleaner 1 is in operation, and the determined amount of electric discharge is different from the present amount of electric discharge, then the generation unit 2 changes the present amount of electric discharge to the determined amount of electric discharge, and then discharges an electric current. When the air cleaner 1 is in operation, and the determined amount of electric discharge is equal to the present amount of electric discharge, the generation unit 2 maintains the present amount of electric discharge, and discharges an electric current.

In step S3, when the control unit 5 determines the amount of electric discharge by the generation unit 2, the control unit 5 controls the air-sending device 31 such that the air-sending device 31 delivers air (step S4). Note that when the air-sending device 31 is in a state of stopping operation, for example, at the start-up of the air cleaner 1, then the air-sending device 31 starts operation to deliver air. The control unit 5 controls operation of the air-sending device 31 such that the air-sending device 31 delivers a specified air volume appropriate to generation and conveyance of the discharge products DP. When the air cleaner 1 is in operation, the air-sending device 31 continues operation to deliver air.

After the generation unit 2 starts electric discharge based on the amount of electric discharge determined by the control unit 5, a predetermined set time has elapsed since the start of electric discharge (step S5), and then the estimation unit 4 determines that the amount of dust in the space S is the third estimation amount, and thus there is a "small" amount of dust in the space S (step S6). The predetermined set time is, for example, "30 minutes", which is a period of time required for 5 μm-particles to settle down, as described above. Note that the set time is not limited to "30 minutes." The set time is determined depending on the area of the space S or the environmental and other conditions. The set time is measured by the time measuring unit 8.

After the generation unit 2 starts electric discharge based on the amount of electric discharge determined by the control unit 5, a predetermined set time has elapsed since the start of electric discharge (step S5), and the estimation unit 4 determines that there is a "small" amount of dust (step S6). Then, the control unit 5 determines the amount of electric discharge by the generation unit 2 (step S7). The amount of electric discharge to be determined in step S7 is predetermined as a second amount of electric discharge when there is a "small" amount of dust. For example, at the second amount of electric discharge, there is a small amount of dust and thus the amount of the ions D1 decreases at a low rate. Consequently, while the ozone generation amount is equivalent to the ozone generation amount at the first amount of electric discharge, the ion generation amount is reduced relative to the ion generation amount at the first amount of electric discharge. Due to these generation amounts as described above, the ratio between the discharge products that reach the target becomes optimum possible for adequate sterilization performance and inactivation performance. The air cleaner 1 produces and emits the discharge products DP when there is a small amount of dust in the space S. This inhibits the discharge products DP from being attenuated by contact of the discharge products DP with the dust, and can thus reduce unnecessary consumption of the discharge products DP.

In step S7, when the control unit 5 determines the amount of electric discharge by the generation unit 2, the control unit 5 controls the generation unit 2 such that the generation unit 2 changes the present amount of electric discharge to discharge an electric current based on the determined amount of electric discharge (step S8). In step S7, when the control unit 5 determines the amount of electric discharge by the generation unit 2, the control unit 5 controls the air-sending device 31 such that the air-sending device 31 continues operation and delivers air (step S8). The control unit 5 controls operation of the air-sending device 31 such that the air-sending device 31 delivers a specified air volume appropriate to generation and conveyance of the discharge products DP. In step S8, when the generation unit 2 discharges an electric current and the air-sending device 31 delivers air, then the electric-discharge control flow ends.

Figure 6:
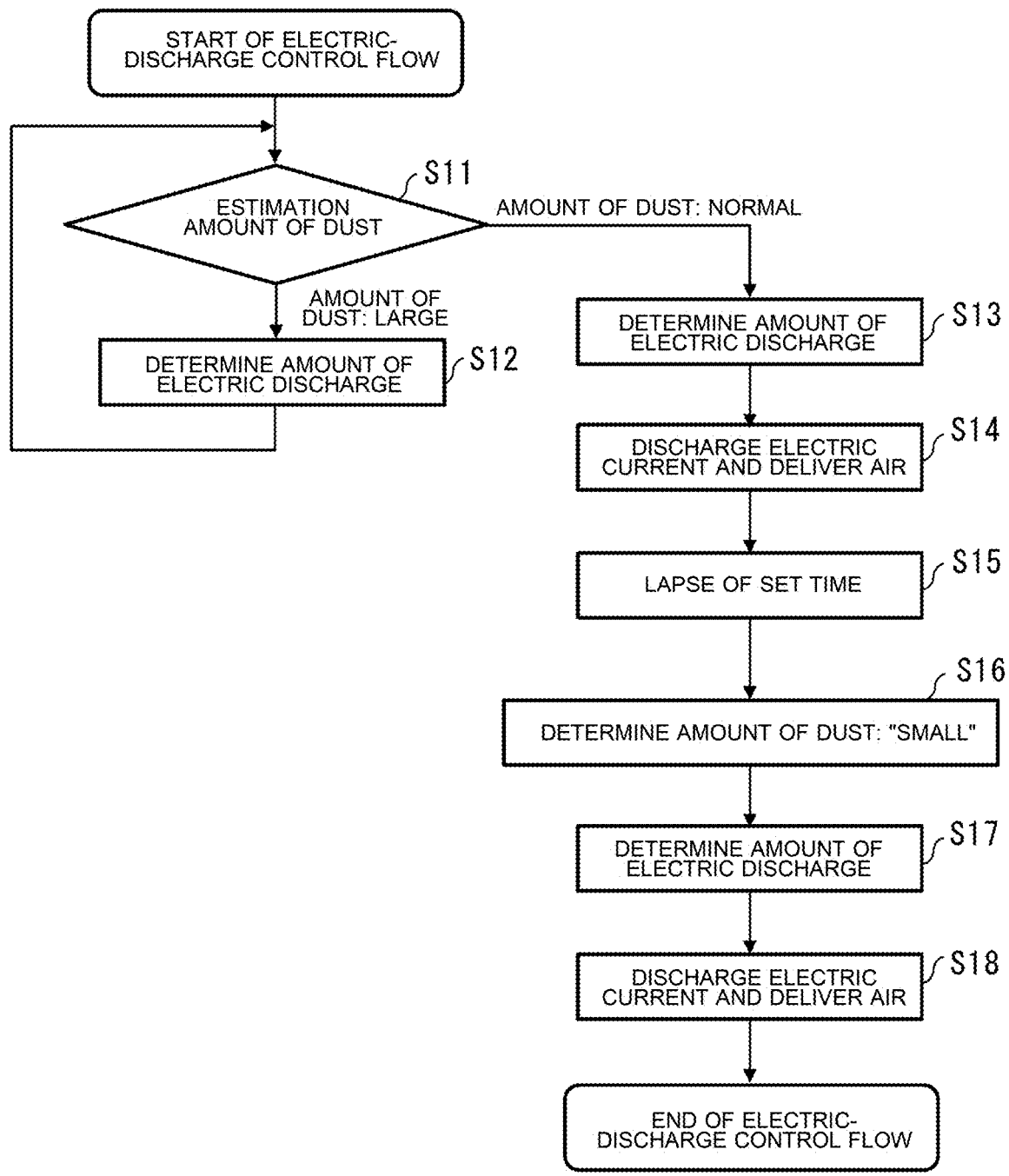
FIG. 6 is a flowchart illustrating another operation of the air cleaner according to Embodiment 1.

FIG. 6 is a flowchart illustrating another operation of the air cleaner 1 according to Embodiment 1. FIG. 6 is a flowchart illustrating operation of the air cleaner 1 that can vary the generation ratio between a plurality of types of discharge products DP by use of the plurality of discharge electrodes 21 as illustrated in FIG. 2. Note that it is possible to switch the control mode for the operation illustrated in FIG. 5 to a control mode for another operation illustrated in FIG. 6, and a user can select either the control mode illustrated in FIG. 5 or the control mode illustrated in FIG. 6. The control unit 5 in the air cleaner 1 controls generation of the discharge products DP according to the amount of dust in the space S as described above.

When an electric-discharge control flow starts, the estimation unit 4 estimates the amount of dust in the space S where the air cleaner 1 is installed (step S11). As described above, the amount of dust may be estimated by comparing the amount of dust measured by the dust sensor 9 with the predetermined threshold, or may be estimated based on the operating condition of the air cleaner itself or the additional device 110.

For example, the electric-discharge control flow starts when the air cleaner 1 starts up. Note that the timing at which the electric-discharge control flow starts is not limited to the start-up of the air cleaner 1. For example, the air cleaner 1 may start the electric-discharge control flow when a user issues a command to start the electric-discharge control flow by pressing a switch during operation of the air cleaner 1. For another example, the air cleaner 1 may start the electric-discharge control flow at a predetermined certain time. The air cleaner 1 may start the electric-discharge control flow, for example, on an hourly basis or at predetermined time intervals.

In step S11, when the estimation unit 4 determines that the amount of dust in the space S is the second estimation amount, and thus there is a "large" amount of dust in the space S, then the control unit 5 controls the devices in the following manner to determine the amount of electric discharge (step S12). The control unit 5 increases the amount of the ions D1 to be generated relative to the amount of the ions D1 to be emitted when the amount of dust is determined as "normal" or "small" to compensate for the decreased amount of the ions D1 due to bonding with the dust. The control unit 5 controls the air volume of the air-sending device 31 that pairs up with the discharge electrode 21*b*, from which a high ratio of the ozone D2 is generated, such that the air volume remains unchanged from the air volume when there is a "normal" or "small" amount of dust. Furthermore, the control unit 5 controls the air volume of the air-sending device 31 that pairs up with the discharge electrode 21*a*, from which a high ratio of the ions D1 is generated, such that the air volume increases relative to the air volume when there is a "normal" or "small" amount of dust, thereby to increase the amount of the ions D1 to be generated in the generation unit 2.

In step S11, when the estimation unit 4 determines that the amount of dust in the space S is the first estimation amount, and thereafter determines that the amount of dust in the space S is the fourth estimation amount, and thus there is a "normal" amount of dust in the space S, then the control unit 5 determines the amount of electric discharge by the generation unit 2 (step S13). The amount of electric discharge to be determined in step S13 is predetermined as a first amount of electric discharge when there is a "normal" amount of dust. In step S13, when the control unit 5 determines the amount of electric discharge by the generation unit 2, the control unit 5 controls the generation unit 2 such that the generation unit 2 discharges an electric current based on the determined amount of electric discharge (step S14).

Note that when the generation unit 2 is in a state of stopping electric discharge, for example, at the start-up of the air cleaner 1, then the generation unit 2 starts electric discharge based on the determined amount of electric discharge and discharges an electric current. When the air cleaner 1 is in operation, and the determined amount of electric discharge is different from the present amount of electric discharge, then the generation unit 2 changes the present amount of electric discharge to the determined amount of electric discharge, and then discharges an electric current. When the air cleaner 1 is in operation, and the determined amount of electric discharge is equal to the present amount of electric discharge, the generation unit 2 maintains the present amount of electric discharge, and discharges an electric current.

In step S13, when the control unit 5 determines the amount of electric discharge by the generation unit 2, the control unit 5 controls the air-sending device 31 such that the air-sending device 31 delivers air (step S14). Note that when the air-sending device 31 is in a state of stopping operation, for example, at the start-up of the air cleaner 1, then the air-sending device 31 starts operation to deliver air. The control unit 5 controls operation of the air-sending device 31 such that the air-sending device 31 delivers a specified air volume appropriate to generation and conveyance of the discharge products DP. When the air cleaner 1 is in operation, the air-sending device 31 continues operation to deliver air.

After the generation unit 2 starts electric discharge based on the amount of electric discharge determined by the control unit 5, a predetermined set time has elapsed since the start of electric discharge (step S15), and then the estimation unit 4 determines that the amount of dust in the space S is the third estimation amount, and thus there is a "small" amount of dust in the space S (step S16). The predetermined set time is, for example, "30 minutes", which is a period of time required for 5 µm-particles to settle down, as described above. Note that the set time is not limited to "30 minutes." The set time is determined depending on the area of the space S or the environmental and other conditions. The set time is measured by the time measuring unit 8.

After the generation unit 2 starts electric discharge based on the amount of electric discharge determined by the control unit 5, a predetermined set time has elapsed since the start of electric discharge (step S15), and the estimation unit 4 determines that there is a "small" amount of dust (step S16). Then, the control unit 5 determines the amount of electric discharge by the generation unit 2 (step S17). The amount of electric discharge to be determined in step S17 is predetermined as a second amount of electric discharge when there is a "small" amount of dust. For example, at the second amount of electric discharge, there is a small amount of dust and thus the amount of the ions D1 decreases at a low rate. Consequently, while the ozone generation amount is equivalent to the ozone generation amount at the first amount of electric discharge, the ion generation amount is reduced relative to the ion generation amount at the first amount of electric discharge. Due to these generation amounts as described above, the ratio between the discharge products that reach the target becomes optimum possible for adequate sterilization performance and inactivation performance. The air cleaner 1 produces and emits the discharge products DP when there is a small amount of dust in the space S. This inhibits the discharge products DP from being attenuated by contact of the discharge products DP with the dust, and can thus reduce unnecessary consumption of the discharge products DP.

More specifically, there is a small amount of dust and thus the amount of the ions D1 is unlikely to decrease. Consequently, when a specified amount of the ions D1 that is predetermined for the treatment target is generated, an excessive amount of the ions D1 is supplied. The control unit 5 thus controls and decreases the amount of the ions D1 to be generated relative to the amount of the ions D1 to be generated when there is a "normal" or "large" amount of dust.

In step S17, when the control unit 5 determines the amount of electric discharge by the generation unit 2, the control unit 5 controls the generation unit 2 such that the generation unit 2 changes the present amount of electric discharge to discharge an electric current based on the determined amount of electric discharge (step S18). In step S17, when the control unit 5 determines the amount of electric discharge by the generation unit 2, the control unit 5 controls the air-sending device 31 such that the air-sending device 31 continues operation and delivers air (step S18). The control unit 5 controls operation of the air-sending device 31 such that the air-sending device 31 delivers a specified air volume appropriate to generation and conveyance of the discharge products DP.

The control unit 5 controls the air volume of the air-sending device 31 that pairs up with the discharge electrode 21b, from which a high ratio of the ozone D2 is generated, such that the air volume remains unchanged from the air volume when there is a "normal" or "large" amount of dust. The control unit 5 decreases the air volume of the air-sending device 31 that pairs up with the discharge electrode 21a, from which a high ratio of the ions D1 is generated, relative to the air volume when there is a "normal" or "large" amount of dust, thereby to decrease the amount of the ions D1 to be generated in the generation unit 2. In step S18, when the generation unit 2 discharges an electric current and the air-sending device 31 delivers air, then the electric-discharge control flow ends.

[Operational Effects of Air Cleaner 1]

The air cleaner 1 includes the estimation unit 4 configured to estimate the amount of dust in the space S, and the control unit 5 configured to control the generation amount of a plurality of types of the discharge products DP to be generated from the generation unit 2 based on the amount of dust estimated by the estimation unit 4. The air cleaner 1 controls the generation amount of the plurality of types of the discharge products DP according to the amount of dust in the space S, and thereby can prevent the discharge products DP from being unnecessarily consumed. With this operation, the air cleaner 1 can prevent a reduction of the discharge products DP present in the space S, and can exhibit adequate sterilization performance and inactivation performance.

The estimation unit 4 estimates the amount of dust in the space S based on the amount of dust measured by the dust sensor 9. The air cleaner 1 includes the dust sensor 9, and detects the amount of dust by use of the dust sensor 9, so that the air cleaner 1 can accurately detect the amount of dust.

The estimation unit 4 estimates the amount of dust in the space S based on the operating condition of the air cleaner 1 itself. The air cleaner 1 can estimate the amount of dust in the space S without use of the dust sensor 9 configured to measure the amount of dust, so that it is possible to reduce the number of components that make up the air cleaner 1, and consequently facilitate manufacturing of the air cleaner 1. In the air cleaner 1, it is possible to reduce the number of components that make up the air cleaner 1, and consequently reduce the manufacturing costs, material costs, and other costs.

The estimation unit 4 estimates the amount of dust in the space S based on the detection of whether a person is present by the human-presence sensor 19. The air cleaner 1 can determine whether the space S is in a state where dust floats based on the detection of whether a person is present in the space S by the human-presence sensor 19, and thereby estimate the amount of dust floating in the space S.

In the air cleaner system 100, the estimation unit 4 in the air cleaner 1 estimates the amount of dust in the space S based on information on the operating condition of the additional device 110 received through the communication modules 50. Alternatively, in the air cleaner system 100, the estimation unit 4 in the air cleaner 1 receives the information on the amount of dust measured by the second dust sensor 9a through the communication modules 50 and estimates the amount of dust in the space S. The air cleaner system 100 can extend the detection area for the amount of dust in cooperation with the additional device 110.

In the air-conditioning apparatus 70, air supplied by the air-sending unit 3 passes through the heat exchanger 71. The air-conditioning apparatus 70 supplies a plurality of types of the discharge products DP to the space S, by use of conditioned air passing through the heat exchanger 71. The air-conditioning apparatus 70 allows the above effects of the air cleaner 1 to be produced, and can perform air-conditioning in the space S, such as temperature regulation and humidity regulation.

Embodiment 2

Figure 7:
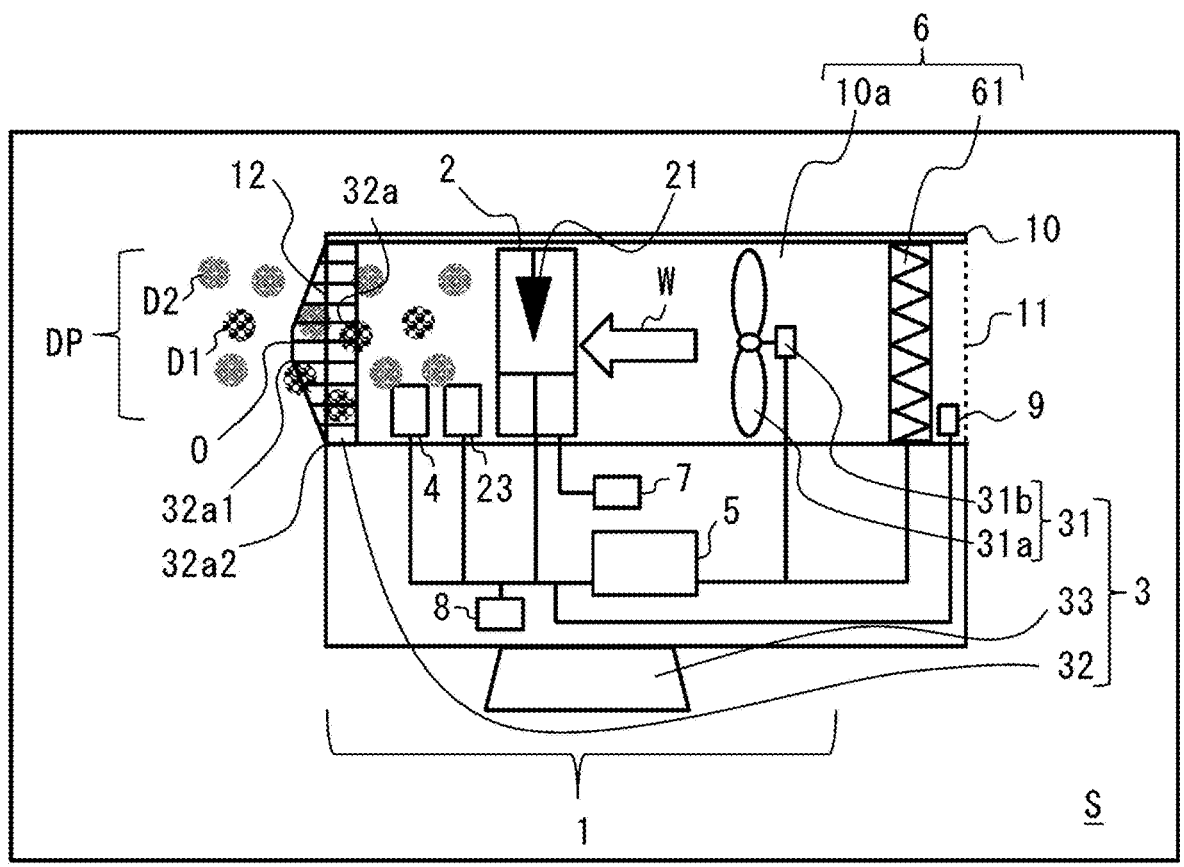
FIG. 7 is a schematic diagram illustrating an example of a relationship between an air cleaner according to Embodiment 2 and a space where the air cleaner is installed.

FIG. 7 is a schematic diagram illustrating an example of a relationship between the air cleaner 1 according to Embodiment 2 and the space S where the air cleaner 1 is installed. The air cleaner 1 according to Embodiment 2 is described below with reference to FIG. 7. Note that the same constituent elements as those of the air cleaner 1 according to Embodiment 1 are denoted by the same reference signs, and descriptions of the same constituent elements are omitted unless otherwise needed. Hereinafter, the air cleaner 1 according to Embodiment 2 will be described, mainly focusing on the different points from Embodiment 1. The air cleaner 1 according to Embodiment 2 is different from the air cleaner 1 according to Embodiment 1 in that the air cleaner 1 includes a collecting mechanism 6.

The air cleaner 1 according to Embodiment 2 includes the collecting mechanism 6 configured to collect dust in the space S to reduce the amount of dust in the space S. The collecting mechanism 6 includes a capturing unit 61 and the air passage 10a. The capturing unit 61 filters the air flowing in the air passage 10a to collect dust contained in the air. Note that the air passage 10a may be included in the casing 10 as its constituent element, and in this case, the collecting mechanism 6 is composed of the capturing unit 61. The capturing unit 61 can be any device configured to collect dust in the air. The capturing unit 61 is, for example, a filter.

In the air passage 10a, the air-sending device 31 is located. The air-sending device 31 allows the air in the air passage 10a to be conveyed. The generation unit 2 is provided also in the same air passage 10a in which the capturing unit 61 and the air-sending device 31 are located. The generation unit 2 is supplied with air having been cleaned by the capturing unit 61.

Note that while the filter is exemplified as the capturing unit 61, the capturing unit 61 is not limited to the filter. The capturing unit 61 may be a cyclone dust collecting mechanism, an electrical dust collecting mechanism, or other type of dust collecting mechanism.

Similarly to the air cleaner 1 according to Embodiment 1, in the air cleaner 1 according to Embodiment 2, the estimation unit 4 estimates the amount of dust in the space S where the air cleaner 1 is installed, and the control unit 5 controls the generation unit 2 according to the estimated amount of dust to control the generation amount of the discharge products DP.

When the estimation unit 4 determines that there is a "small" amount of dust in the space S, the control unit 5 controls operation of the air-sending device 31 in the air-sending unit 3 to deliver a specified air volume appropriate to generation and conveyance of the discharge products DP.

When the estimation unit 4 determines that there is a "normal" amount of dust in the space S, the control unit 5 also controls operation of the air-sending device 31 in the air-sending unit 3 to deliver a specified air volume appropriate to generation and conveyance of the discharge products DP.

The air cleaner 1 according to Embodiment 2 includes the capturing unit 61. Due to this configuration, the time required for the estimation unit 4 to determine that there is a "small" amount of dust after determining that there is a "normal" amount of dust is calculated from the area of the space S, the air volume of the air-sending device 31 during operation, and the collecting rate of the capturing unit 61. The time derived from this calculation, that is, the time required for the estimation unit 4 to determine that there is a "small" amount of dust after determining that there is a "normal" amount of dust is shorter than 30 minutes.

When the estimation unit 4 determines that there is a "large" amount of dust, the control unit 5 controls the generation unit 2 to stop generating the discharge products DP, while continuing operation of the air-sending device 31 to capture the dust through the capturing unit 61 to reduce the amount of dust present in the space S. When the estimation unit 4 estimates that there is a large amount of dust in the space S, the control unit 5 performs dust removing operation to collect dust through the capturing unit 61 in the collecting mechanism 6. The air cleaner 1 according to Embodiment 2 exercises the control in this manner, and thus can reduce the amount of floating dust and efficiently generate the discharge products DP.

Note that the air cleaner 1 according to Embodiment 2 has the configuration in which the capturing unit 61 and the generation unit 2 are located in the same air passage 10a, and the air-sending unit 3 delivers air to the generation unit 2, however, the air cleaner 1 is not limited to this configuration.

Figure 8:
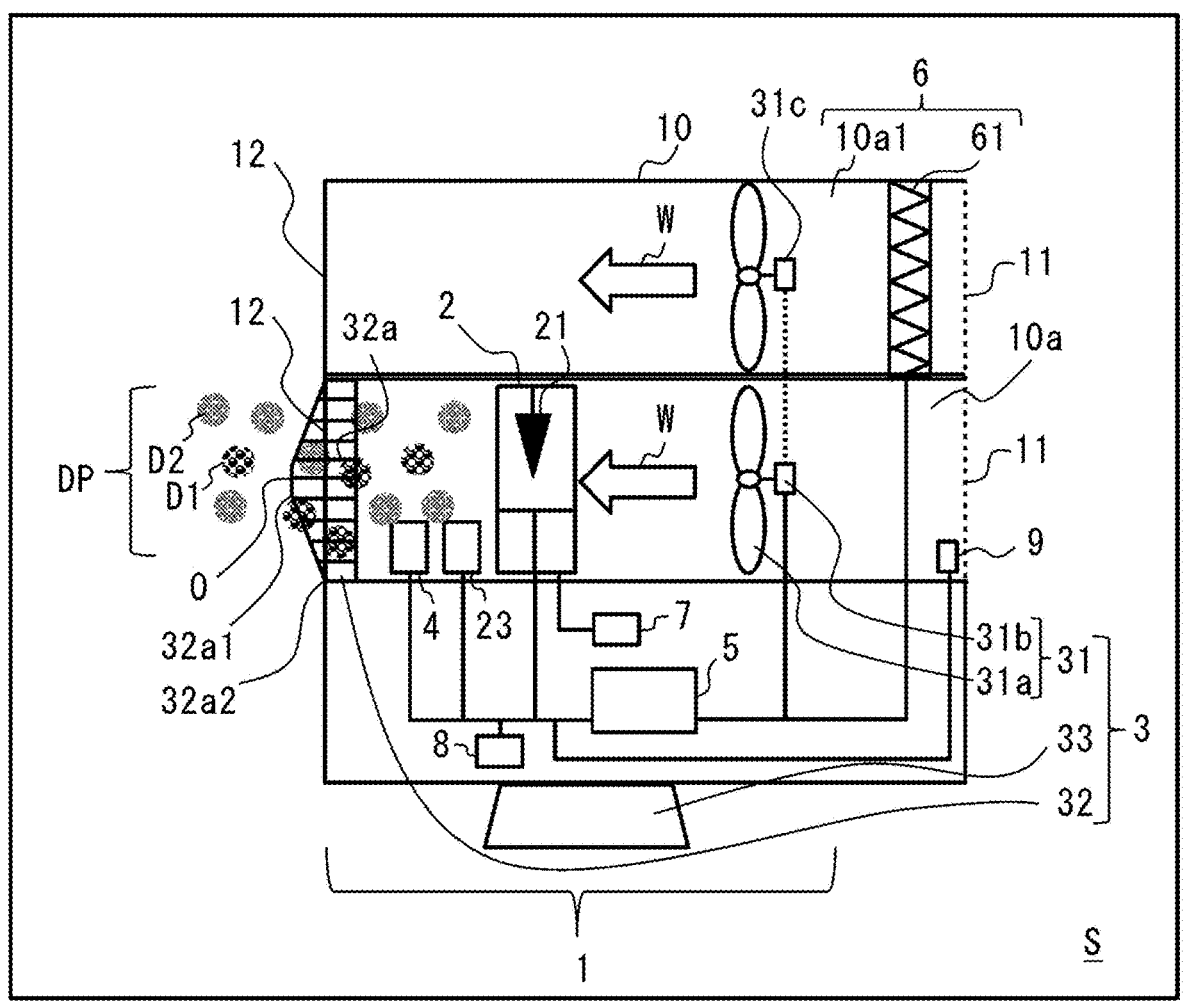
FIG. 8 is a schematic diagram illustrating another example of a structure of the air cleaner according to Embodiment 2.

FIG. 8 is a schematic diagram illustrating another example of a structure of the air cleaner 1 according to Embodiment 2. The air cleaner 1 may include the casing 10 in which the air passage 10a and a second air passage 10a1 are formed, and a second air-sending device 31c configured to form a flow of air. In the air passage 10a, the generation unit 2 is located. In the second air passage 10a1, the capturing unit 61 of the collecting mechanism 6 is located. In Embodiment 2, the collecting mechanism 6 includes the capturing unit 61 and the second air passage 10a1. The capturing unit 61 filters the air flowing in the second air passage 10a1 to collect dust contained in the air. Note that the second air passage 10a1 may be included in the casing 10 as its constituent element, and in this case, the collecting mechanism 6 is composed of the capturing unit 61. The second air-sending device 31c is controlled by the control unit 5 and thus the air volume is regulated. The air cleaner 1 according to Embodiment 2 may have a plurality of combinations each formed by the second air passage 10a1 and the second air-sending device 31c.

In the air cleaner 1 according to Embodiment 2, the air-sending device 31 is located in the air passage 10a, while the second air-sending device 31c is located in the second air passage 10a1. That is, the air cleaner 1 includes a plurality of air-sending devices as illustrated in FIG. 8, in which the air-sending device configured to deliver air to the generation unit 2 is separate from the air-sending device configured to deliver air to the collecting mechanism 6. In the air cleaner 1 according to Embodiment 2, the second air passage 10a1 in which the capturing unit 61 is located is provided separately from the air passage 10a in which the generation unit 2 is located. These air-sending devices located in the separate air passages 10a1 and 10a perform air-sending operation. In this case, the air-sending devices located in the separate air passages may operate differently from each other according to the amount of dust in the space S.

For example, when the estimation unit 4 determines that there is a "small" amount of dust, the air-sending device 31 operates, which is located in the air passage 10a in which the generation unit 2 is provided, while the second air-sending device 31c stops, which is located in the second air passage 10a1 in which the capturing unit 61 is provided. The air cleaner 1 according to Embodiment 2 exercises the control in this manner, and thus allows the discharge products DP to be present in the space S efficiently.

When the estimation unit 4 determines that there is a "normal" amount of dust, the air-sending device 31 operates, which is located in the air passage 10a in which the generation unit 2 is provided, while the second air-sending device 31c also operates, which is located in the second air passage 10a1 in which the capturing unit 61 is provided. The air cleaner 1 according to Embodiment 2 exercises the control in this manner, and thus allows the discharge products DP to be generated while reducing the amount of floating dust.

When the estimation unit 4 determines that there is a "large" amount of dust, the air-sending device 31 stops, which is located in the air passage 10a in which the generation unit 2 is provided, while the air-sending device 31 operates, which is located in the second air passage 10a1 in which the capturing unit 61 is provided. The air cleaner 1 according to Embodiment 2 exercises the control in this manner, and thus can reduce the amount of floating dust and prevent the discharge products DP from being unnecessarily consumed.

While controlling generation of the discharge products DP according to the amount of dust in the space S, the air cleaner 1 according to Embodiment 2 can remove dust such as powder dirt in the room more quickly and can generate the discharge products DP more efficiently, compared to when the air cleaner 1 does not include the capturing unit 61.

Figure 9:
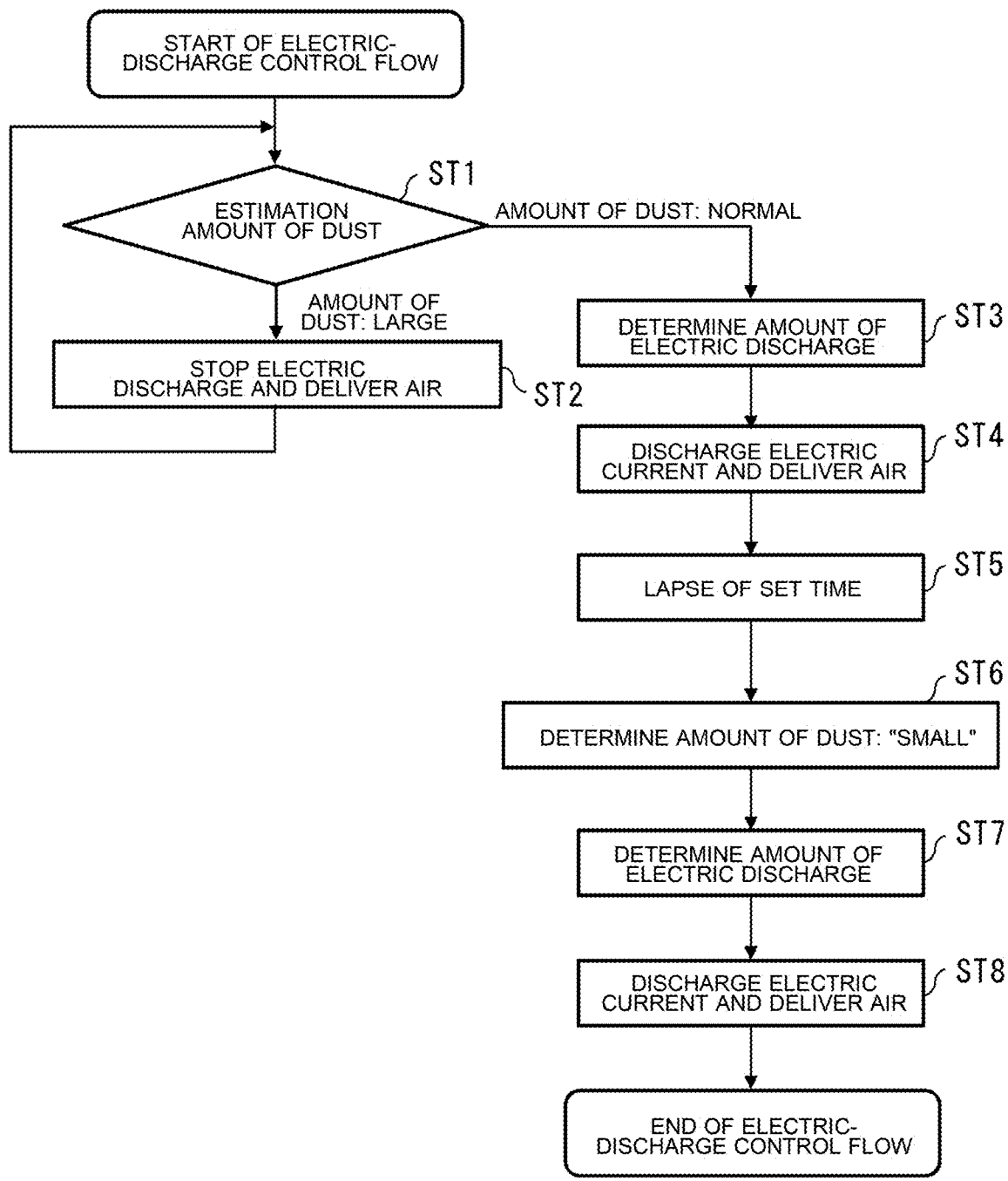
FIG. 9 is a flowchart illustrating operation of the air cleaner according to Embodiment 2.

FIG. 9 is a flowchart illustrating operation of the air cleaner 1 according to Embodiment 2. The control unit 5 in the air cleaner 1 according to Embodiment 2 controls generation of the discharge products DP according to the amount of dust in the space S as described above. With reference to FIG. 9, an example of the control is described below in which the control unit 5 controls generation of the discharge products DP according to the amount of dust in the space S.

When an electric-discharge control flow starts, the estimation unit 4 estimates the amount of dust in the space S where the air cleaner 1 is installed (step ST1).

In step ST1, when the estimation unit 4 determines that the amount of dust in the space S is the second estimation amount, and thus there is a "large" amount of dust in the space S, then the control unit 5 controls the generation unit 2 to stop electric discharge (step ST2). Electric discharge is stopped in the generation unit 2, and thus emission of the discharge products DP from the generation unit 2 is stopped. Note that when the generation unit 2 is in a state of stopping electric discharge, for example, at the start-up of the air cleaner 1, this state is maintained. When the air cleaner 1 is in operation, electric discharge from the generation unit 2 is stopped.

In step ST1, when the estimation unit 4 determines that there is a "large" amount of dust in the space S, the control unit 5 controls the air-sending device 31 such that the air-sending device 31 delivers air (step ST2). Note that when the air-sending device 31 is in a state of stopping operation, for example, at the start-up of the air cleaner 1, then the air-sending device 31 starts operation to deliver air. When the air cleaner 1 is in operation, the air-sending device 31 continues operation to deliver air. The air cleaner 1 according to Embodiment 2 exercises the control in this manner, and thus can reduce the amount of floating dust even when electric discharge is stopped, and efficiently generate the discharge products DP when the electric discharge is started.

In step ST1, when the estimation unit 4 determines that the amount of dust in the space S is the first estimation amount, and thereafter determines that the amount of dust in the space S is the fourth estimation amount, and thus there is a "normal" amount of dust in the space S, then the control unit 5 determines the amount of electric discharge by the generation unit 2 (step ST3). The amount of electric discharge to be determined in step ST3 is predetermined as a first amount of electric discharge when there is a "normal" amount of dust. In step ST3, when the control unit 5 determines the amount of electric discharge by the generation unit 2, the control unit 5 controls the generation unit 2 such that the generation unit 2 discharges an electric current based on the determined amount of electric discharge (step ST4).

Note that when the generation unit 2 is in a state of stopping electric discharge, for example, at the start-up of the air cleaner 1, then the generation unit 2 starts electric discharge based on the determined amount of electric discharge and discharges an electric current. When the air cleaner 1 is in operation, and the determined amount of electric discharge is different from the present amount of electric discharge, then the generation unit 2 changes the present amount of electric discharge to the determined amount of electric discharge, and then discharges an electric current. When the air cleaner 1 is in operation, and the determined amount of electric discharge is equal to the present amount of electric discharge, the generation unit 2 maintains the present amount of electric discharge, and discharges an electric current.

In step ST3, when the control unit 5 determines the amount of electric discharge by the generation unit 2, the control unit 5 controls the air-sending device 31 such that the air-sending device 31 delivers air (step ST4). Note that when the air-sending device 31 is in a state of stopping operation, for example, at the start-up of the air cleaner 1, then the air-sending device 31 starts operation to deliver air. The control unit 5 controls operation of the air-sending device 31 such that the air-sending device 31 delivers a specified air volume appropriate to generation and conveyance of the discharge products DP. When the air cleaner 1 is in operation, the air-sending device 31 continues operation to deliver air.

After the generation unit 2 starts electric discharge based on the amount of electric discharge determined by the control unit 5, a predetermined set time has elapsed since the start of electric discharge (step ST5), and then the estimation unit 4 determines that the amount of dust in the space S is the third estimation amount, and thus there is a "small" amount of dust in the space S (step ST6). The lapse of set time is measured by the time measuring unit 8.

After the generation unit 2 starts electric discharge based on the amount of electric discharge determined by the control unit 5, a predetermined set time has elapsed since the start of electric discharge (step ST5), and the estimation unit 4 determines that there is a "small" amount of dust (step ST6). Then, the control unit 5 determines the amount of electric discharge by the generation unit 2 (step ST7). The amount of electric discharge to be determined in step ST7 is predetermined as a second amount of electric discharge when there is a "small" amount of dust.

In step ST7, when the control unit 5 determines the amount of electric discharge by the generation unit 2, the control unit 5 controls the generation unit 2 such that the generation unit 2 changes the present amount of electric discharge to discharge an electric current based on the determined amount of electric discharge (step ST8). In step ST7, when the control unit 5 determines the amount of electric discharge by the generation unit 2, the control unit 5 controls the air-sending device 31 such that the air-sending device 31 continues operation and delivers air (step ST8). The control unit 5 controls operation of the air-sending device 31 such that the air-sending device 31 delivers a specified air volume appropriate to generation and conveyance of the discharge products DP. In step ST8, when the generation unit 2 discharges an electric current and the air-sending device 31 delivers air, then the electric-discharge control flow ends.

[Operational Effects of Air Cleaner 1]

When the estimation unit 4 estimates that there is a large amount of dust in the space S, the control unit 5 performs dust removing operation to collect dust through the capturing unit 61 in the collecting mechanism 6. The air cleaner 1 according to Embodiment 2 exercises the control in this manner to reduce the amount of dust floating in the space S, and consequently can prevent attenuation of the discharge products DP in the space S and thus prevent the discharge products DP from being unnecessarily consumed.

The air cleaner 1 includes a plurality of air-sending units 3 in which the air-sending unit 3 configured to deliver air to the generation unit 2 is separate from the air-sending unit 3 configured to deliver air to the collecting mechanism. The air cleaner 1 has the configuration described above, and can thus generate and spray the discharge products DP to the space S, while reducing the amount of floating dust.

The configurations described in the foregoing embodiments are mere examples of the present disclosure. Combining these configurations with other publicly known techniques is possible, and partial omissions and modifications of the configurations are possible without departing from the gist of the present disclosure.

REFERENCE SIGNS LIST

1: air cleaner, 2: generation unit, 3: air-sending unit, 4: estimation unit, 5: control unit, 6: collecting mechanism, 7: high-voltage conversion unit, 8: time measuring unit, 9: dust sensor, 9a: second dust sensor, 10: casing, 10a: air passage, 10a1: second air passage, 11: air inlet, 12: air outlet, 19: human-presence sensor, 19a: second human-presence sensor, 21: discharge electrode, 21a: discharge electrode, 21b: discharge electrode, 23: measurement unit, 31: air-sending device, 31a: fan, 31b: motor, 31c: second air-sending device, 32: grille, 32a: fin, 32a1: inner end portion, 32a2: outer end portion, 33: drive device, 50: communication module, 51: communication harness, 61: capturing unit, 70: air-conditioning apparatus, 71: heat exchanger, 100: air cleaner system, 110: additional device, DP: discharge product, O: center, S: space, W: air-sending direction, O: center

The invention claimed is:

1. An air cleaner comprising:
a plurality of generation circuits each configured to perform electric discharge by being applied with a high voltage, and each generate a plurality of types of discharge products, the plurality of generation circuits having different characteristics of generation of the plurality of types of discharge products, at least one type of the plurality of types of discharge products bonding with dust and an amount of the at least one type of the plurality of types of discharge products accordingly decreasing;

an air-sending device configured to form a flow of air, and spray the plurality of types of discharge products generated from at least one of the plurality of generation circuits to a space;

an estimation circuit configured to estimate an amount of dust floating in the space by selecting whether an amount of dust floating in the space is a first estimation amount smaller than a predetermined threshold or is a second estimation amount larger than or equal to the predetermined threshold and larger than the first estimation amount; and a control circuit configured to control a generation amount of the plurality of types of discharge products to be generated from each of the plurality of generation circuits having different characteristics of generation of the plurality of types of discharge products based on the amount of dust estimated by the estimation circuit, the control circuit being configured to exercise control in which, when the estimation circuit estimates that the amount of dust is the first estimation amount, the plurality of generation circuits perform the electric discharge, and, when the estimation circuit estimates that the amount of dust exceeds the first estimation amount and is the second estimation amount larger than the first estimation amount, the plurality of generation circuits stop the electric discharge.

2. The air cleaner of claim 1, further comprising a dust sensor configured to measure the amount of dust in the space, wherein the estimation circuit is configured to estimate the amount of dust in the space based on the amount of dust measured by the dust sensor.

3. The air cleaner of claim 1, further comprising a human-presence sensor configured to detect whether a person is present in the space, wherein the estimation circuit is configured to estimate the amount of dust in the space based on detection of whether a person is present by the human-presence sensor.

4. The air cleaner of claim 1, wherein the estimation circuit is configured to estimate the amount of dust in the space based on an operating condition of the air cleaner itself.

5. The air cleaner of claim 1, comprising:

a plurality of the air-sending devices provided corresponding to the plurality of generation circuits and capable of delivering different volumes of air to the plurality of respective generation circuits, wherein the control circuit is configured to vary the generation amount of the discharge products to be emitted to an exterior of a device by use of different volumes of air to be delivered to the plurality of respective generation circuits according to the amount of dust estimated by the estimation circuit.

6. The air cleaner of claim 1, further comprising a collecting mechanism configured to collect dust in the space, wherein the control circuit is configured to perform dust removing operation to collect dust in the collecting mechanism when the estimation circuit estimates that the amount of dust floating in the space is the second estimation amount.

7. The air cleaner of claim 6, wherein the collecting mechanism is a filter, and the control circuit is configured to operate the air-sending device to collect the dust in the filter during the dust removing operation when the estimation circuit estimates that the amount of dust floating in the space is the second estimation amount.

8. The air cleaner of claim 6, further comprising:

a casing in which an air passage and a second air passage are formed, at least one of the plurality of generation circuits being located in the air passage, the collecting mechanism being located in the second air passage; and a second air-sending device configured to form a flow of air, wherein the air-sending device is located in the air passage, and the second air-sending device is located in the second air passage.

9. An air cleaner system comprising:

the air cleaner of claim 1; and an additional device located in the space in which the air cleaner is located, wherein the air cleaner and the additional device include respective communication modules through which the air cleaner and the additional device are allowed to communicate with each other, and the estimation circuit is configured to estimate the amount of dust in the space based on information on an operating condition of the additional device received through the communication modules.

10. An air cleaner system comprising:

the air cleaner of claim 1; and an additional device located in the space in which the air cleaner is located, wherein the air cleaner and the additional device include respective communication modules through which the air cleaner and the additional device are allowed to communicate with each other, the additional device further includes a second dust sensor configured to measure the amount of dust in the space, and the estimation circuit is configured to receive information on the amount of dust measured by the second dust sensor through the communication modules and estimate the amount of dust in the space.

11. An air-conditioning apparatus comprising:

the air cleaner of claim 1; and a heat exchanger configured to exchange heat between refrigerant flowing inside the heat exchanger and air that is present around the heat exchanger, wherein air supplied by the air-sending device passes through the heat exchanger, and the air-conditioning apparatus is configured to supply the plurality of types of discharge products to the space, by use of conditioned air passing through the heat exchanger.

* * * * *